United States Patent [19]

Deguchi et al.

[11] Patent Number: 5,395,742
[45] Date of Patent: Mar. 7, 1995

[54] DIAMINOSTILBENE SERIES COMPOUND AND A METHOD FOR FORMING AN IMAGE USING THE SAME

[75] Inventors: Yasuaki Deguchi; Toshiaki Kubo, both of Minami-ashigara, Japan

[73] Assignee: Fuji Photo Film Co., Ltd., Kanagawa, Japan

[21] Appl. No.: 243,175

[22] Filed: May 16, 1994

[30] Foreign Application Priority Data

May 18, 1993 [JP] Japan ................... 5-138999

[51] Int. Cl.$^6$ .............................................. G03C 5/10
[52] U.S. Cl. ..................... 430/429; 430/393; 430/434; 430/455; 430/460; 430/461; 430/463; 430/486; 430/933
[58] Field of Search ............... 430/393, 429, 434, 455, 430/460, 461, 463, 486, 933

[56] References Cited

U.S. PATENT DOCUMENTS

| | | | |
|---|---|---|---|
| 4,232,112 | 11/1980 | Kuse ..................... | 430/486 |
| 4,895,786 | 1/1990 | Kurematsu et al. ................ | 430/428 |
| 5,043,253 | 8/1991 | Ishikawa ............................ | 430/933 |

FOREIGN PATENT DOCUMENTS 62-257154  11/1987  Japan.
4249243   9/1992  Japan.

*Primary Examiner*—Hoa Van Le
*Attorney, Agent, or Firm*—Birch, Stewart, Kolasch & Birch

[57] ABSTRACT

There is disclosed a novel diaminostilbene series compound, a method for forming an image using the same, and a composition comprising the same. The diaminostilbene compound is represented by the following formula (I):

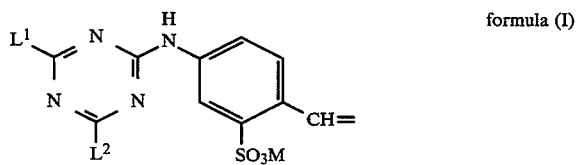

formula (I)

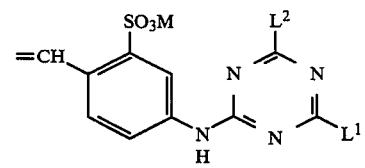

wherein

L$^1$ and L$^2$, which are the same or different, each represent —OR$^1$ or —N—R$^2$(R$^3$), wherein the four substituents L$^1$ and L$^2$ have four or more substituents in total selected from substituents represented by the following formula (II);

R$^1$ and R$^2$ each represent a hydrogen atom, an alkyl group, or an alkyl group having a substituent selected from substituents represented by the formula (II);

R$^3$ represents an alkyl group or an alkyl group having a substituent selected from substituents represented by the formula (II); and M represents a hydrogen atom, an alkali metal, an ammonium, or a pyridinium:

formula (II)
—SO$_3$M, —OSO$_3$M, —COOM, and —NR$_3$X wherein
X represents a halogen atom,
R represents an alkyl group, and
M has the same meaning as M in formula (I).

10 Claims, No Drawings

DIAMINOSTILBENE SERIES COMPOUND AND A METHOD FOR FORMING AN IMAGE USING THE SAME

FIELD OF THE INVENTION

The present invention relates to a novel diaminostilbene series compound that can be used in photographic processing. The present invention also relates to a method for forming an image using a silver halide photographic material and a diaminostilbene series compound. In particular, the present invention relates to a photographic processing composition that does not bring about crystallization during the storage of the composition; and relates to a method for processing a silver halide photographic material by using the processing composition. More particularly, the present invention relates to a method for forming an image that can provide an image of high quality whose white background is little colored.

BACKGROUND OF THE INVENTION

Silver halide photographic materials, such as color photographic materials, including color negative films and color prints, are generally processed by an automatic processor that is operated according to running processing in a photofinishing laboratory. The demand of the market is that results are to be returned to customers in a short period of time. Therefore, processing steps including the development processing step have been tried to make easy and rapid.

However, making the processing easy and rapid, specifically, lowering the replenishment rate and shortening the processing time, lead to problems of the image formed, such as an increase in the minimum density due to residual color and deterioration of preservability of the image.

Generally, silver halide color photographic materials to be used for color negative films and color prints have photosensitive layers of multilayer constitution containing three types of silver halide emulsions applied on a support. These silver halide emulsions contain sensitizing dyes respectively so that they may be spectrally sensitive to blue light, green light, and red light.

Generally, sensitizing dyes in photographic materials are dissolved out in the processing steps, but, if the processing time is shortened, the dissolving out of sensitizing dyes is not carried out satisfactorily. As a result, large amounts of sensitizing dyes left in the photographic material make the image, particularly the white background, colored, thereby making the image unacceptable for satisfactory appreciation. Therefore, a processing composition and a method for forming an image that can solve the problem caused by the residual color are strongly demanded.

To solve the problem, it is known that the residual color due to sensitizing dyes can be lessened to some extent by adding a water-soluble fluorescent whitening agent to a developer, a bleach-fix solution, or a washing/stabilizing bath, which is described, for example, in Research Disclosure No. 20733. Further, for example, JP-A ("JP-A" means unexamined published Japanese patent application) No. 257154/1987 discloses a method wherein a specific sensitizing dye and a specific fluorescent whitening agent are used, and JP-A No. 249243/1992 discloses a method wherein a specific water-soluble fluorescent whitening agent is used.

The methods described in JP-A Nos. 257154/1987 and 249243/1992 are more favorable than the prior art in that residual color is lessened to some extent. However, in these conventionally known techniques that use a water-soluble fluorescent whitening agent, the effect is unsatisfactory when the processing is made rapid at a low-replenishing-rate; and also an increase in the concentration of the fluorescent whitening agent in the processing solution, to obtain a satisfactory whitening effect, results in a problem that deposition of the fluorescent whitening agent occurs during the storage. Although, among the conventional fluorescent whitening agents, compounds that do not cause depositing and that are good in preservability are known, these compounds do not have any effect to reduce residual color or deteriorate the effect of reducing residual color.

The method disclosed in JP-A No. 249243/1992 is more favorable than the prior art in that residual color is reduced to some extent. However, when the inventors tried to conduct rapid processing at a low-replenishing-rate using these prior techniques, the following problems took place: as processing was made easy and rapid, the effect of improving residual color was reduced, and when the processing solution was stored at a low temperature, the fluorescent whitening agent in the processing solution caused depositing.

SUMMARY OF THE INVENTION

Therefore, the first object of the present invention is to provide a novel diaminostilbene series compound.

The second object of the present invention is to provide a method for forming an image, in which method in a rapid development processing, when a processing solution for the processing is stored at a low temperature, the fluorescent whitening agent does not cause depositing and after the development processing, an image excellent in whiteness due to a satisfactory fluorescent whitening effect and reduction in residual color can be obtained.

Other and further objects, features, and advantages of the invention will appear more evident from the following description.

DETAILED DESCRIPTION OF THE INVENTION

The present inventors have studied keenly and have discovered that a bistriazinyl-2,2'-diaminostilbene compound having certain specific substituents does not cause depositing when stored at a low temperature. Further, the inventors have surprisingly found that, when continuous processing, which is made easy and rapid at a low-replenishing-rate, is carried out in the presence of the diaminostilbene compound using the method of the present invention for forming an image, the method for forming an image is very effective against color contamination due to residual color, which contamination was conventionally unsatisfactorily dealt with. That is, the present invention provides:

(1) A diaminostilbene compound represented by the following formula (I):

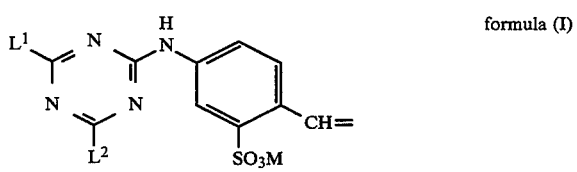

formula (I)

-continued

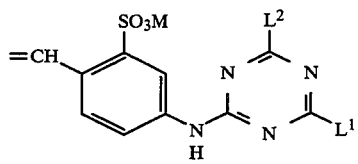

wherein
- $L^1$ and $L^2$, which are the same or different, each represent $-OR^1$ or $-N-R^2(R^3)$, wherein the four substituents $L^1$ and $L^2$ have four or more substituents in total selected from the group consisting of substituents represented by the following formula (II);
- $R^1$ and $R^2$ each represent a hydrogen atom, an alkyl group, or an alkyl group having a substituent selected from the group consisting of substituents represented by the following formula (II);
- $R^3$ represents an alkyl group or an alkyl group having a substituent selected from the group consisting of substituents represented by the following formula (II); and
- M represents a hydrogen atom, an alkali metal, an ammonium, or a pyridinium:

formula (II)
$-SO_3M$, $-OSO_3M$, $-COOM$, and $-NR_3X$ wherein
- X represents a halogen atom,
- R represents an alkyl group, and
- M has the same meaning as M in formula (I);

(2) A method for forming an image, in which method, after a silver halide photographic material having a photosensitive silver halide emulsion layer on at least one side of a support is exposed to light imagewise, the silver halide photographic material is subjected to a developing step, a desilvering step, a washing and/or stabilizing step, and then the material is dried, which comprises at least one step of the above processing steps being carried out in the presence of at least one compound represented by the above formula (I);

(3) The method for forming an image as stated in the above (2), wherein a color developer containing, as a color developing agent, a compound represented by the following formula (D) is used in the developing step:

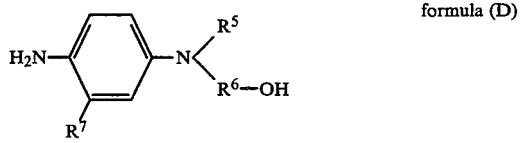

formula (D)

wherein
- $R^5$ represents a straight-chain or branched-chain alkyl group having 1 to 6 carbon atoms, or a straight-chain or branched-chain hydroxylalkyl group having 3 to 6 carbon atoms;
- $R^6$ represents a straight-chain or branched-chain alkylene group having 3 to 6 carbon atoms, or a straight-chain or branched-chain hydroxylalkylene group having 3 to 6 carbon atoms; and
- $R^7$ represents a hydrogen atom, a straight-chain or branched-chain alkyl group having 1 to 4 carbon atoms, or a straight-chain or branched-chain alkoxy group having 1 to 4 carbon atoms;

(4) A composition for development processing for a silver halide photographic material, which comprises a compound represented by the above formula (I).

Formula (I) is described in more detail below.

In Formula (I), $L^1$ and $L^2$, which are the same or different, each represent $-OR^1$ or $-N-R^2(R^3)$, in which $R^1$ and $R^2$, which are the same or different, each represent a hydrogen atom or an alkyl group, $R^3$ represents an alkyl group. The alkyl groups represented by $R^1$, $R^2$, and $R^3$ are the same or different. The alkyl group is a straight-chain or branched-chain alkyl group, whose hydrogen atom may be substituted with another substituent. The substituent being capable of substitution with a hydrogen atom is preferably a hydrophilic group. Particularly preferably, in the present invention $R^1$, $R^2$, and $R^3$ each represent an alkyl group having a strong hydrophilic group selected from the group consisting of groups represented by the formula (II). Preferably the alkyl group has 1 to 10 carbon atoms, more preferably 1 to 5 carbon atoms.

In formulas (I) and (II), M represents a hydrogen atom, an alkali metal (e.g., Na and K), an ammonium including one having alkyl group(s) as a substituent whose alkyl group has preferably 1 to 10 carbon atoms (e.g., ammonium, monoalkylammonium, dialkylammonium, trialkylammonium, and tetraalkylammonium such as tetramethylammonium), and a pyridinium (which may have substituents, e.g. pyridinium and alkylpyridinium such as methylpyridinium). In formula (II), X represents a halogen atom (e.g., Cl, Br, and I), R represents an alkyl group (e.g., methyl and ethyl).

In the present invention, the substituents $L^1$ and $L^2$ of the compound represented by formula (I) have the above features and specific examples of $L^1$ and $L^2$ include a methoxy group, an ethoxy group, a propoxy group, an isopropoxy group, a butoxy group, an isobutoxy group, a pentyloxy group, a hexyloxy group, a methylamino group, an ethylamino group, a propylamino group, an isopropylamino group, a butylamino group, an isobutylamino group, a 2-hydroxyethoxy group, a 3-hydroxypropoxy group, a 4-hydroxybutoxy group, a 2-hydroxyethylamino group, a 3-hydroxypropylamino group, a 4-hydroxybutylamino group, a 2-hydroxyethylethylamino group, a 3-hydroxypropylpropylamino group, a 4-hydroxybutylbutylamino group, a dimethylamino group, a diethylamino group, a dipropylamino group, a diisopropylamino group, a dibutylamino group, diisobutylamino group, a di-2-hydroxyethylamino group, a di-3-hydroxypropylamino group, a dihydroxybutylamino group, a 2-sulfoethoxy group, a 3-sulfopropoxy group, a 4-sulfobutoxy group, a 2-sulfoethylamino group, a 3-sulfopropylamino group, a 4-sulfobutylamino group, a di-2-sulfoethylamino group, a di-3-sulfopropylamino group, a di-4-sulfobutylamino group, a 2-sulfoethylmethylamino group, a 3-sulfopropylmethylamino group, a 4-sulfobutylmethylamino group, a 2-sulfoethylethylamino group, a 3-sulfopropylethylamino group, a 4-sulfobutylethylamino group, a carboxymethoxy group, a 2-carboxyethoxy group, a 3-carboxypropoxy group, a 4-carboxybutoxy group, a carboxymethylamino group, a 2-carboxyethylamino group, a 3-carboxypropylamino group, a 4-carboxybutylamino group, a di-2-carboxyethylamino group, a di-3-carboxypropylamino group, a di-4-carboxybutylamino group, a 2-carboxyethylmethylamino group, a 3-carboxypropylmethylamino group, a 4-carboxybutylmethylamino group, a 2-carboxyethylethylamino group, a 3-carboxypropylethylamino group, a 4-carboxybutylethylamino group, a 2-sulfoxyethoxy group, a 3-sulfoxypropoxy group, a 4-sulfoxybutoxy group, a 2-sulfoxyethylamino group, a 3-sulfoxypropylamino group, a 4-sulfoxybutylamino group, a di-2-sulfoxyethylamino group, a di-3-sulfoxypropylamino group, a di-4-sulfoxybutylamino group, a 2-sulfoxyethylmethylamino group, a 3-sulfoxypropylmethylamino group, a 4-sulfoxybutylmethylamino group, a 2-sulfoxyethylethylamino group, a 3-sulfoxypropylethylamino group, a 4-sulfoxybutylethylamino group, a trimethylammoniomethylamino group, a trimethylammonioethylamino group, a trimethylammoniopropylamino group, a triethylammoniomethylamino group, a triethylammonioethylamino group, and a triethylammoniopropylamino group.

More preferably, they are, for example, a methoxy group, an ethoxy group, a 2-hydroxyethoxy group, a 2-hydroxyethylamino group, a 2-sulfoethylamino group, a di-2-sulfoethylamino group, a 2-carboxyethylamino group, a di-2-carboxyethylamino group, and a di-2-hydroxyethylamino group.

The more hydrophilic the compound of formula (I) in the present invention is, the more preferable it is. Specifically, the compound of formula (I) has a value of log P of from $-30$ or more to $-4$ or below, more preferably from $-18$ or more to $-7$ or below. Herein the term "value of log P" refers to the value defined as the value of the logarithm of the distribution ratio P (= [concentration in octanol]/[concentration in water]) of an octanol/water binary system of the particular compound. If the value of log P is too small, the effect of lowering residual color is lowered, while if the value of log P is too large, it is not preferable because, for example, the fluorescent whitening agent cause depositing.

The processing method of the present invention is effective for any process for the development processing for a photographic material containing a silver halide emulsion. The method is particularly effective when color negative films and color papers are processed; it is more preferably effective when the replenishing rate is low, and it is particularly preferably effective when a color photographic paper containing a high-silver-chloride emulsion is processed rapidly at a low-replenishing-rate (e.g., of a color developer).

The low-replenishing-rate in the process in the present invention varies depending on the type of the photographic material and, for example, when usual color photographic papers are developed, the total replenishment rate of all the steps is preferably 60 to 500 ml/m$^2$, more preferably 90 to 200 ml/m$^2$. Preferably the total replenishment rate of all the steps is 90 to 200 ml/m$^2$ or less, and preferably the total replenishment rate of the bleach/fix step and the washing and/or stabilizing step is 60 to 150 ml/m$^2$. Further, for example, in development processing of general color negative films, the total replenishment rate of all the steps is preferably 90 to 1,000 ml/m$^2$, more preferably 90 to 500 ml/m$^2$.

In a method for processing a color print photographic material, particularly a color photographic paper and the like, the present invention is preferable if the silver halide emulsion contained in the photographic material is high in silver chloride content; specifically, if the silver halide emulsion contained in the photographic material is 95 mol % or more in silver chloride content.

The compound of formula (I) for use in the present invention has four substituents L having four or more substituents in total, selected from the group consisting of substituents represented by formula (II). Herein, the number of substituents represented by formula (II) is preferably an even number, and it is preferably 8 or less, more preferably 6 or less. Specific structures are those of diaminostilbene compounds having substituents shown in the following Table.

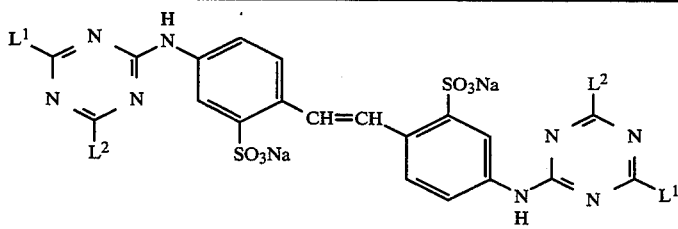

| Compound No. | L$^1$ | L$^2$ |
|---|---|---|
| SR-1 | —OC$_2$H$_4$SO$_3$Na | —OC$_2$H$_4$SO$_3$Na |
| SR-2 | —OC$_2$H$_4$OSO$_3$Na | —OC$_2$H$_4$OSO$_3$Na |
| SR-3 | —N(C$_2$H$_4$OSO$_3$Na)$_2$ | —N(C$_2$H$_4$OSO$_3$Na)$_2$ |
| SR-4 | —OC$_2$H$_4$SO$_3$H | —OC$_2$H$_4$SO$_3$H |
| SR-5 | —NHC$_2$H$_4$SO$_3$H | —NHC$_2$H$_4$SO$_3$H |
| SR-6 | —NHC$_2$H$_4$SO$_3$(NH$_4$) | —NHC$_2$H$_4$SO$_3$(NH$_4$) |
| SR-7 | —NHC$_2$H$_4$COOH | —NHC$_2$H$_4$COOH |
| SR-8 | " | —NHC$_2$H$_4$SO$_3$Na |
| SR-9 | —NHC$_2$H$_4$COONa | —NHC$_2$H$_4$COONa |
| SR-10 | " | —NHC$_2$H$_4$SO$_3$Na |
| SR-11 | —N(CH$_3$)$_3$Cl | —N(CH$_3$)$_3$Cl |
| SR-12 | —NHC$_2$H$_4$OSO$_3$Na | —NHC$_2$H$_4$OSO$_3$Na |
| SR-13 | —NHC$_2$H$_4$SO$_3$Na | —NHC$_2$H$_4$SO$_3$Na |

-continued

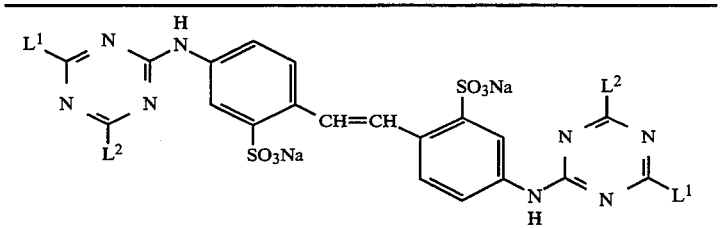

| Compound No. | L¹ | L² |
|---|---|---|
| SR-14 | $-N(CH_3)(C_2H_4SO_3Na)$ | $-N(CH_3)(C_2H_4SO_3Na)$ |
| SR-15 | $-N(C_2H_5)(C_2H_4SO_3Na)$ | $-N(C_2H_5)(C_2H_4SO_3Na)$ |
| SR-16 | $-N(C_2H_4SO_3Na)_2$ | $-N(C_2H_4SO_3Na)_2$ |
| SR-17 | $-N(C_2H_4SO_3Na)_2$ | $-OCH_3$ |
| SR-18 | " | $-OC_2H_5$ |
| SR-19 | " | $-OC_2H_4OH$ |
| SR-20 | " | $-N(C_2H_5)_2$ |
| SR-21 | " | $-NHC_2H_4OH$ |
| SR-22 | " | $-OC_2H_4NH_2$ |
| SR-23 | " | $-NHC_2H_4N(CH_3)_2$ |
| SR-24 | $-NHC_2H_4SO_3Na$ | $-OC_2H_4SO_3Na$ |
| SR-25 | " | $-N(CH_3)(C_2H_4SO_3Na)$ |
| SR-26 | " | $-N(C_2H_4OSO_3Na)_2$ |
| SR-27 | " | $-NHC_2H_4COONa$ |
| SR-28 | $-NHCH_2COONa$ | $-NHCH_2COONa$ |
| SR-29 | $-NH(CH_2)_3COONa$ | $-NH(CH_2)_3COONa$ |
| SR-30 | $-OCH_2COONa$ | $-OCH_2COONa$ |
| SR-31 | $-N(CH_2COONa)_2$ | $-N(CH_2COONa)_2$ |
| SR-32 | $-NHCH_2COONa$ | $-NHCH_2CH_2SO_3Na$ |

The object of the present invention can be attained by adding the compound of formula (I) to any of the processing solutions of (1) a developing step, (2) a desilvering step, and (3) a washing and/or stabilizing step, and preferably by adding the compound of formula (I) to the processing solutions of several steps. Herein "a desilvering step" means any one of steps of bleaching, fixing, and bleach-fixing, and a combination of the steps.

In the present invention, the compound of formula (I) is preferably added, out of all the processing steps, to the frontmost-possible processing solution, and particularly preferably it is used by adding it to a developer (a color developer or a black-and-white developer).

The preferable concentration of the compound of formula (I) in the processing solution is $5 \times 10^{-5}$ to $1 \times 10^{-2}$ mol/liter, more preferably $1 \times 10^{-4}$ to $5 \times 10^{-3}$ mol/liter, in the running solution, while in a replenishing solution, it is preferably a concentration needed to keep the concentration of the running solution at a predetermined concentration; that is, specifically 1.5 to $10^{-4}$ to $1.5 \times 10^{-2}$ mol/liter.

By "a development processing composition" of the present invention is meant a processing composition required to develop a silver halide photographic material, and specifically the development processing composition of the present invention includes, for example, a developing solution, a fixing solution, a bleaching solution, a bleach-fix solution, a washing solution, or a stabilizing solution that contains a compound of formula (I).

The composition may be prepared as a solution having a concentration to be used as it is, or it may be prepared as a concentrate. Also the composition may be a powder (in the form of granules or powders).

The compound may be used in a photographic material. In that case, the amount of the composition to be used is equimolar to or 2 to 3 times the amount of the sensitizing dye.

In the above cases, the concentration of the compound of formula (I) in the composition is equal to or higher than the concentration of it to be used.

The compound of formula (I) can be synthesized by a conventionally known process. For example, it can be synthesized by condensing 4,4'-diaminostilbene-2,2'-disulfonic acid and cyanuric chloride, to synthesize 4,4'-bistriadinylaminostilbene-2,2'-disulfonic acid, followed by condensing it with an alcohol or an amine. Specifically, there is a process described in *Kogyo Kagaku Zasshi*, Vol. 60, No. 5, page 604 (1957).

Synthetic Examples of fluorescent whitening agents are shown below:

Synthesis of Compound (SR-13)

10.2 Grams of cyanuric chloride was dissolved in 100 ml of acetone, and then 100 g of 10% aqueous sodium diaminostilbenesulfonate solution was added dropwise thereto over 20 min with cooling with ice, during which the pH of the reaction solution was kept at 5 to 7 using an aqueous sodium carbonate solution. After the reaction solution was stirred for 30 min, 100 g of 18% aqueous taurine solution was added. Thereafter, the acetone was distilled off and the reaction solution was stirred for 3 hours with the internal temperature being kept at 95° C., during which the pH of the reaction solution was kept at or over 6 using an aqueous sodium carbonate solution. After the completion of the reaction, the reaction solution was cooled and was subjected to salting out, to obtain 12 g of light yellow crystals. The product was confirmed to be Compound (SR-13) from the mass spectrum and NMR.

$\lambda max = 348$ nm ($\epsilon = 4.65 \times 10^4$, $H_2O$)

Synthesis of Compound (SR-25)

10.2 Grams of cyanuric chloride was dissolved in 100 ml of acetone, and then 100 g of 10% aqueous sodium diaminostilbenesulfonate solution was added dropwise over 20 min with cooling with ice, during which the pH of the reaction solution was kept at 5 to 7 using an aqueous sodium carbonate solution. After the reaction solution was stirred for 30 min, the internal temperature was elevated to 40° C., and 35 g of a 18% aqueous taurine solution was added. After the reaction solution was heated for 1 hour, the acetone was distilled off, then 50 g of a 20% aqueous N-methyltaurine solution was added, the internal temperature was elevated to 95° C., and the reaction solution was stirred for 3 hours, during which the pH of the reaction solution was kept at or over 6 using an aqueous sodium carbonate solution. After the completion of the reaction, the reaction solution was cooled and was subjected to salting out, to obtain 8.3 g of light yellow crystals. The product was confirmed to be Compound (SR-25) from the mass spectrum and NMR.

$\lambda max = 345$ nm ($\epsilon = 4.38 \times 10^4$, $H_2O$)

Other compounds and comparative compounds were synthesized in the same manner as performed above.

| Compound | State of compound | $\lambda$ max |
|---|---|---|
| (SR-1) | Light yellow powder | 351 nm ($\epsilon = 5.10 \times 10^4$, $H_2O$) |
| (SR-2) | " | 352 nm ($\epsilon = 5.33 \times 10^4$, $H_2O$) |
| (SR-3) | " | 348 nm ($\epsilon = 4.51 \times 10^4$, $H_2O$) |
| (SR-4) | " | 351 nm ($\epsilon = 5.23 \times 10^4$, $H_2O$) |
| (SR-5) | " | 348 nm ($\epsilon = 4.78 \times 10^4$, $H_2O$) |
| (SR-6) | " | 348 nm ($\epsilon = 4.76 \times 10^4$, $H_2O$) |
| (SR-7) | " | 343 nm ($\epsilon = 4.86 \times 10^4$, $H_2O$) |
| (SR-8) | " | 345 nm ($\epsilon = 4.56 \times 10^4$, $H_2O$) |
| (SR-9) | " | 343 nm ($\epsilon = 4.43 \times 10^4$, $H_2O$) |
| (SR-10) | " | 345 nm ($\epsilon = 4.99 \times 10^4$, $H_2O$) |
| (SR-11) | " | 357 nm ($\epsilon = 4.25 \times 10^4$, $H_2O$) |
| (SR-12) | " | 343 nm ($\epsilon = 5.11 \times 10^4$, $H_2O$) |
| (SR-14) | " | 352 nm ($\epsilon = 5.68 \times 10^4$, $H_2O$) |
| (SR-15) | " | 353 nm ($\epsilon = 5.40 \times 10^4$, $H_2O$) |
| (SR-16) | " | 350 nm ($\epsilon = 4.98 \times 10^4$, $H_2O$) |
| (SR-17) | " | 349 nm ($\epsilon = 4.76 \times 10^4$, $H_2O$) |
| (SR-18) | " | 348 nm ($\epsilon = 4.77 \times 10^4$, $H_2O$) |
| (SR-19) | " | 349 nm ($\epsilon = 4.62 \times 10^4$, $H_2O$) |
| (SR-20) | " | 352 nm ($\epsilon = 4.91 \times 10^4$, $H_2O$) |
| (SR-21) | " | 351 nm ($\epsilon = 5.21 \times 10^4$, $H_2O$) |
| (SR-22) | " | 350 nm ($\epsilon = 5.18 \times 10^4$, $H_2O$) |
| (SR-23) | " | 352 nm ($\epsilon = 4.63 \times 10^4$, $H_2O$) |
| (SR-24) | " | 350 nm ($\epsilon = 4.78 \times 10^4$, $H_2O$) |
| (SR-26) | " | 349 nm ($\epsilon = 5.12 \times 10^4$, $H_2O$) |
| (SR-27) | " | 353 nm ($\epsilon = 4.56 \times 10^4$, $H_2O$) |

The compound of formula (I) is effective in the case wherein it is used alone and also effective in the case wherein it is used in combination with sufficient amount of other diaminostilbene series compounds. Compounds with which the compound of formula (I) will be used in combination are preferably diaminostilbene compounds represented by the following formula (III):

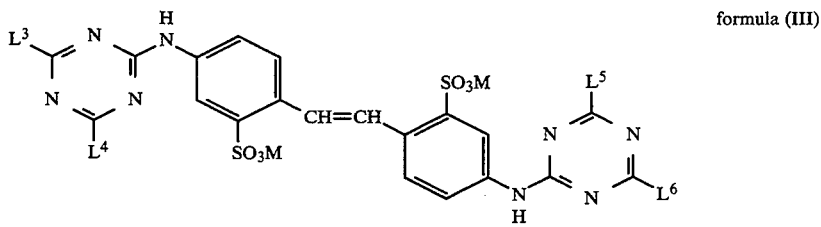

formula (III)

wherein $L^3$, $L^4$, $L^5$, and $L^6$, which are the same or different, each represent —$OR^8$ or —N—$R^9(R^{10})$, wherein $R^8$, $R^9$, and $R^{10}$ each represent a hydrogen atom, an alkyl group, a substituted alkyl group, or an alkyl group having a substituent selected from the group consisting of substituents represented by the following formula (IV), and M represents a hydrogen atom, an alkali metal, an ammonia, or a pyridinium, as defined in the formulas (I) and (II), wherein four substituents $L^3$, $L^4$, $L^5$, and $L^6$ do not have four or more substituents in total, selected from the group consisting of substituents represented by the above formula (IV).

formula (IV)

—$SO_3M$, —$OSO_3M$, —COOM, —$NR_3X$ wherein

X represents a halogen atom,

R represents an alkyl group, and

M has the same meaning as M in formula (III). Those have the same meaning as defined in the formula (I) and (II).

The compound represented by formula (III) includes specifically the compounds shown in the following Table.

known or commercially available diaminostilbene series fluorescent whitening agent can be used. As the commercially available compounds, for example, those described in *Senshoku Note,* Vol. 19 (Shikisen-sha), pages 165 to 168, can be mentioned, and among them Whitex RP or Whitex BRF liq. is preferable.

The photographic material of the present invention is described in detail below.

In the photographic material of the present invention, preferably a dye capable of being decolored by processing, as described in European Patent EP 0337490A2, pages 27 to 76 (particularly an oxonol dye and a cyanine dye), is added to a hydrophilic colloid layer, in order, for example, to prevent irradiation or halation or to improve safelight immunity. Particularly, as dyes that hardly cause color separation or hardly degrade safelight immunity, even if the amount thereof to be used is increased, water-soluble dyes described in JP-A No. 310139/1991 are preferred. As the coating amount of these water-soluble dyes, the following coating amounts can be used as guides:

Cyan dyes: 20 to 100 mg/m$^2$

Magenta dyes: 0 to 50 mg/m$^2$

Yellow dyes: 0 to 30 mg/m$^2$

In the present invention, preferably, as described above, a colored layer containing a solid fine powder

| Compound No. | L$^3$ | L$^4$ | L$^5$ | L$^6$ |
|---|---|---|---|---|
| B-1 | —NHC$_2$H$_4$SO$_3$Na | —OCH$_3$ | —OCH$_3$ | —N(C$_2$H$_4$OH)$_2$ |
| B-2 | —NHC$_2$H$_4$SO$_3$Na | —OCH$_3$ | —OCH$_3$ | —NHC$_2$H$_4$OH |
| B-3 | —NHC$_2$H$_4$SO$_3$Na | —NHC$_2$H$_5$ | —NHC$_2$H$_5$ | —NHC$_2$H$_4$OH |
| B-4 | —NHC$_2$H$_4$OH | —NHC$_2$H$_4$OH | —NHC$_2$H$_4$OH | —NHC$_2$H$_4$OH |
| B-5 | —OC$_2$H$_4$OH | —OC$_2$H$_4$OH | —OC$_2$H$_4$OH | —OC$_2$H$_4$OH |
| B-6 | —OC$_2$H$_4$OH | —OH | —OH | —OC$_2$H$_4$OH |
| B-7 | —OC$_2$H$_4$OH | —NH$_2$ | —NH$_2$ | —OC$_2$H$_4$OH |
| B-8 | —OC$_2$H$_4$OH | —OCH$_3$ | —OCH$_3$ | —OC$_2$H$_4$OH |
| B-9 | —OC$_2$H$_4$OH | —OC$_2$H$_4$NH$_2$ | —OC$_2$H$_4$NH$_2$ | —OC$_2$H$_4$OH |
| B-10 | —NHC$_2$H$_4$OH | —OC$_2$H$_5$ | —OC$_2$H$_5$ | —NHC$_2$H$_4$OH |
| B-11 | —OC$_2$H$_4$OH | —NHC$_2$H$_5$ | —NHC$_2$H$_5$ | —OC$_2$H$_4$OH |
| B-12 | —N(C$_2$H$_5$)(C$_2$H$_4$OH) | —OH | —OH | —N(C$_2$H$_5$)(C$_2$H$_4$OH) |

As the fluorescent whitening agent that can be used in combination with the compound of formula [I], a dye or colloidal silver is applied, and/or a hydrophilic colloid layer is colored with a water-soluble dye.

Preferably, the optical reflection density of unexposed photographic materials for use in the present invention is such that the optical reflection density at the wavelength where the optical reflection density is highest in a visible region having a wavelength of 400 nm to 700 nm is preferably from 0.2 or over to 2.0 or below, more preferably from 0.2 or over to 1.5 or below, and particularly preferably from 0.2 or over to 1.2 or below. The type of the coloring material (e.g., a white pigment, a solid fine particle dye, an antiirradiation dye, and colloidal silver) and the coating amount thereof can be chosen so that these conditions may be satisfied. In a region whose optical reflection density is below 0.2, the effect of the coloring material on the sharpness cannot be substantially expected. Further, in a region whose optical reflection density is 2.0 or over is not practically suitable, because deterioration of the white background due to residual color becomes conspicuous.

In the present invention, optical reflection density is measured by a reflection densitometer generally used in the art and is defined as given below. Incidentally, when the optical reflection density is measured, it is required that a standard reflection plate is placed on the underside of the sample, to prevent an error of measurement due to light that will otherwise pass through the sample.

Optical reflection density = $\log_{10}(F_0/F)$
$F_0$: Reflected luminous flux of the standard white plate
$F$: Reflected luminous flux of the sample The color photographic material according to the present invention can be composed by applying at least one yellow-color-forming silver halide emulsion layer, at least one magenta-color-forming silver halide emulsion layer, and at least cyan-color-forming silver halide emulsion layer on a reflective support. In general color printing paper, color couplers capable of forming dyes complementary to lights to which the silver halide emulsions are sensitive are contained, so that color reproduction can be carried out by the subtractive color process. In general color printing paper, silver halide emulsion grains are spectrally sensitized with a blue-sensitive spectral sensitizing dye, a green-sensitive spectral sensitizing dye, and a red-sensitive spectral sensitizing dye, in the order of the above color-forming layers, respectively, and the color-forming layers are applied on a support in the above-mentioned order, to compose the color printing paper. However the order may be changed. That is, in some cases, in view of rapid processing, it is preferable that the photosensitive layer containing silver halide grains whose average grain size is largest is placed as an uppermost layer and in other cases, in view of the preservability under exposure to light, preferably the lowermost layer is a magenta-color-forming photosensitive layer.

The photosensitive layers and the color-forming hues may not have the above correspondence, and at least one infrared-sensitive silver halide emulsion layer may also be used.

The silver halide grains for use in the above photographic material are made, for example, of silver chloride, silver bromide, silver (iodo)chlorobromide, or silver iodobromide. Particularly, in the present invention, to shorten the development processing time, silver halide grains made of silver chloride or silver chlorobromide substantially free from silver iodide are preferably used. Herein "substantially free from silver iodide" means that the silver iodide content is 1 mol % or below (including 0), preferably 0.2 mol % or below (including 0). On the other hand, in some cases, in order to increase the high illumination intensity sensitivity, to increase the spectral sensitization sensitivity, or to increase the preservability of the photographic material, it is preferable to use high-silver-chloride grains containing 0.01 to 3 mol % of silver iodide in the emulsion surface, as described in JP-A No. 84545/1991. Although the halogen composition of the emulsion may differ from grain to grain, if an emulsion having a halogen composition uniform from grain to grain is used, it is easy to make the properties among the grains homogeneous. Further, with respect to the halogen distribution in the silver halide emulsion grains, for example, grains having the so-called uniform structure wherein the composition is uniform throughout each of the silver halide grains, grains having the so-called layered structure wherein the composition of the core in the silver halide grains is different from that of the shell (that may be composed of a layer or layers) surrounding the core, or grains having a structure wherein the inside or the surface of the grains has nonlayered parts different in halogen composition (if the nonlayered parts are on the surface, the parts different in halogen composition are joined to the edges, the corners, or on the planes) can be suitably chosen and used. In order to obtain a high sensitivity, it is more advantageous to use the later two cases than to use the grains having the uniform structure, which is also preferable in view of the pressure sensitivity properties. If the silver halide grains have the above structures, the boundary between the parts different in halogen composition may be a clear boundary or an unclear boundary where a mixed crystal is formed due to difference in composition or may be a boundary where the structure is continuously changed positively.

In the photographic material to be applied to rapid processing as in the present invention, a so-called high-silver-chloride emulsion that is high in silver halide content is preferably used. In the present invention, the silver chloride content of the high-silver-chloride emulsion is preferably 90 mol % or more, more preferably 95 mol % or more.

Such a high-silver-chloride emulsion has preferably a structure with a silver bromide localized phase present in the silver halide grains and/or on the surface of the silver halide grains in a layered or nonlayered fashion as described above. The halogen composition of the above localized phase is preferably such that the silver bromide content is at least 10 mol %, more preferably over 20 mol %. The silver bromide content of a silver bromide localized phase can be analyzed, for example, by using the X-ray diffraction method (e.g., described in *Shin-jikkenkagaku-koza, 6, Kozokaiseki* edited by Nihon Kagaku-kai and published by Maruzen). The localized phase can be present in the grains or on the edges, corners, or planes on the surface of the grains and an preferable example is that such a localized phase is epitaxially grown on the corners of the grains. It is also effective to increase the silver chloride content of the silver halide emulsion in order to reduce the replenishing rate of the development processing solution. In that case, an emulsion comprising almost pure silver chloride, that is, having a silver chloride content of 98 to 100 mol % is also preferably used.

The average grain size (obtained by assuming the diameters of circles equivalent to the projected areas of grains to be the grain sizes and taking the number average thereof) of silver halide grains contained in the silver halide emulsion used in said photographic material is preferably 0.1 to 2 μm.

Their grain size distribution is preferably a so-called monodisperse distribution having a deviation coefficient (obtained by dividing the standard deviation of the grain size distribution by the average grain size) of 20% or below, desirably 15% or below, and more preferably 10% or below. In this case, in order to obtain a wide latitude, it is also preferable that such monodisperse emulsions are blended to be used in a layer or are applied in layers.

The shape of the silver halide grains contained in the photographic emulsion may be a regular crystal shape, such as a cubic shape, a tetradecahedral shape, or an octahedral shape, an irregular crystal shape, such as a spherical shape and a tabular shape, or a composite crystal shape formed by combining these shapes. The silver halide grains may be made up of silver halide grains having various crystal shapes. In the present invention, in particular, it is recommended that the silver halide grains contain 50% or more, preferably 70% or more, more preferably 90% or more, of grains having the above regular crystal shape.

In addition, an emulsion wherein tabular grains having an average aspect ratio (diameter calculated as a circle/thickness) of 5 or over, preferably 8 or over, amount to, as projected areas, greater than 50% of all the grains can also be preferably used.

The silver bromochloride emulsion for use in the present invention can be prepared by using a process, for example, described by P. Glafkides in *Chemie et Phisique Photographique* (published by Paul Montel, 1967), by G. F. Duffin in *Photographic Emulsion Chemistry* (published by Focal Press, 1966), or by V. L. Zelikman et al. in *Making and Coating Photographic Emulsion* (published by Focal Press, 1964). That is, any of the acid process, the neutralization process, the ammonia process, and the like can be used and, as the way of reacting a soluble silver salt with a soluble halide, any of the single-jet method, the double-jet method, the method of the combination thereof, and the like can be used. The method wherein grains are formed in an atmosphere having excess silver ions (the so-called reverse precipitation method) can also be used. As one type of the double-jet method, a method wherein the pAg in the liquid phase where the silver halide will be formed is kept constant, that is, the so-called controlled double-jet method can also be used. According to this method, a silver halide emulsion wherein the crystal shape is regular and the grain sizes are nearly uniform can be obtained.

Preferably, the localized phase or the substrate of the silver halide grains of the present invention contains different metal ions or their complex ions. Preferable metal ions are chosen from ions or metal complexes of metals belonging to Groups VIII and IIb of the Periodic Table, lead ions, and thallium ions. For the localized phase, mainly, ions, or complex ions, for example, of iridium, rhodium, or iron are chosen, and for the substrate, metal ions or complex ions, for example, of osmium, iridium, rhodium, platinum, ruthenium, palladium, cobalt, nickel, and iron, can be used in combination. The type of metal ions and the concentration of metal ions in the localized phase may be different from those in the substrate. Several of these metals may be used. Particularly preferably an iron compound or an iridium compound is allowed to be present in the silver bromide localized phase.

These metal ion-providing compounds are incorporated into the localized phase and/or other grain part (the substrate) of the silver halide grains of the present invention, for example, by allowing them to be present in an aqueous gelatin solution that will serve as a dispersing medium, an aqueous halide solution, an aqueous silver salt solution, or other aqueous solution at the time when silver halide grains are formed, or by adding silver halide fine particles containing the particular metal ions and dissolving the fine particles.

Incorporation of metal ions for use in the present invention into emulsion grains may be carried out before, during, or immediately after the formation of the grains. The incorporation can be changed depending on where the metal ions are positioned in the grains.

Generally the silver halide emulsion in the photographic material according to the present invention is subjected to chemical sensitization and spectral sensitization.

As the chemical sensitization, chemical sensitization using a chalcogen-sensitizing agent (specifically, e.g., sulfur sensitization, typically by adding an unstable sulfur compound; selenium sensitization, by using a selenium compound; and tellurium sensitization, by using a tellurium compound), noble metal sensitization, represented by gold sensitization, and reduction sensitization can be mentioned, which may be used alone or in combination. As compounds used in the chemical sensitization, those described in JP-A No. 215272/1987, page 18, the right lower column, to page 22, the right upper column, are preferably used.

The emulsion for use in the present invention is of the so-called surface latent image type wherein a latent image is mainly formed on the grain surface.

To the silver halide emulsion for use in the photographic material of the present invention, various compounds or their precursors can be added in order to prevent fogging during the production steps of the photographic material, during the storage, or during the photographic processing, or in order to stabilize the photographic performance. Specific examples of these compounds are described in the above-mentioned JP-A No. 215272/1987, pages 39 to 72, which compounds are preferably used. Also, 5-arylamino-1,2,3,4-thiatriazole compounds (the aryl residue has at least one electron-attracting group), as described in EP 0447647 are preferably used.

Spectral sensitization is carried out for the purpose of giving spectral sensitivity in a desired wavelength region, to the emulsion of each of the layers in the photographic material of the present invention.

In the photographic material according to the present invention, as spectral sensitizing dyes to be used for spectral sensitization in blue, green, and red regions, those described, for example, by F. M. Harmer in *Heterocyclic Compounds-Cyanine Dyes and Related Compounds* (published by John Wiley & Sons [New York, London], 1964) can be mentioned. Specific examples of the compounds and spectral sensitization methods are preferably those described in the above-mentioned JP-A No. 215272/1987, page 22, the right upper column, to page 38, and out of them more preferable compounds are those mentioned as specific compound examples that do not have a carboxyl group in the molecule, i.e., (S-1) to (S-19), (S-21), (S-23) to (S-38), (S-40) to (S-44), (S-46) to (S-48), (S-51), (S-53), (S-55) to (S-58), (S-60), (S-62), (S-63), (S-66), (S-68), (S-71) to (S-83), (S-85) to (S-90), etc. Further, particularly as a red-sensitive spectral sensitizing dye for silver halide emulsion grains high in silver chloride content, a spectral sensitizing dye described in JP-A No. 123340/1991 is very preferable in view, for example, of stability, intensity of the adsorption, and temperature dependence of exposure to light.

In the photographic material of the present invention, if the infrared region is to be spectrally sensitized effectively, sensitizing dyes described in JP-A No. 15049/1991, page 12, the left upper column, to page 21, the left lower column; in JP-A No. 20730/1991, page 4, the left lower column, to page 15, the left lower column; EP-0,420,110, page 4, line 21, to page 6, line 54; in EP-0,420,012, page 4, line 12, to page 10, line 33; in EP-0,443,466, and in U.S. Pat. No. 4,975,362 are preferably used.

In order to incorporate these spectral sensitizing dyes into the silver halide emulsion, they may be directly dispersed into the emulsion or they may be dissolved in a solvent, such as water, methanol, ethanol, propanol, methyl Cellosolve, and 2,2,3,3-tetrafluoropropanol, or a mixture of these solvents, and the solution may be added to the emulsion. Further, as described, for example, in JP-B ("JP-B" means examined Japanese patent publication) Nos. 23389/1969, 27555/1969, and 22089/1982, the spectral sensitizing dyes may be made into an aqueous solution in the presence of an acid or a base; or as described, for example, in U.S. Pat. Nos. 3,822,135 and 4,006,025, they may be formed into an aqueous solution or a colloidal dispersion in the presence of a surface-active agent and it may be added to the emulsion. Further, the spectral sensitizing dyes may be dissolved in a solvent substantially incompatible with water, such as phenoxyethanol, and then they are dispersed in water or a hydrophilic colloid to be added to the emulsion. Further, as described in JP-A Nos. 102733/1978 and 105141/1983, the spectral sensitizing dyes may be directly dispersed in a hydrophilic colloid, and the dispersion may be added to the emulsion. The timing of the addition to the emulsion may be at any stage of the preparation of emulsions known to be useful conventionally. That is, the timing of the addition may be before or during the formation of grains of the silver halide emulsion, between the time immediately after the formation of grains and the time before the washing step, before or during the chemical sensitization, between the time immediately after the chemical sensitization and the time when the emulsion is cooled and solidified, or at the time when a coating solution is prepared. Although, most generally, the addition is carried out after the completion of the chemical sensitization but before the application, the spectral sensitizing dye can be added simultaneously with a chemical sensitizing dye, to carry out the spectral sensitization and the chemical sensitization at the same time, as described in U.S. Pat. Nos. 3,628,969 and 4,225,666; or the spectral sensitizing dye can be added prior to the chemical sensitization, as described in JP-A No. 113928/1983; or it can be added before the completion of the formation of the precipitation of silver halide grains to start the spectral sensitization. Further, as taught in U.S. Pat. No. 4,225,666, the spectral sensitizing dye can be added in portions; that is, part of the spectral sensitizing dye can be added prior to the chemical sensitization, and the rest can be added after the chemical sensitization, and thus the spectral sensitizing dye can be added at any time during the formation of the silver halide grains, as taught in U.S. Pat. No. 4,183,756. Among the above techniques, the technique wherein the sensitizing dye is added before the washing step of the emulsion or before the chemical sensitization, is preferable.

The amount of the spectral sensitizing dyes to be added varies over a wide range according to the situation, and the amount is preferably in the range of $0.5 \times 10^{-6}$ mol to $1.0 \times 10^{-2}$ mol, more preferably in the range of $1.0 \times 10^{-6}$ to $5.0 \times 10^{-3}$ mol, per mol of the silver halide.

In the photographic material of the present invention, if a sensitizing dye having a spectral sensitizing sensitivity particularly from the red region to the infrared region is used, it is preferable to additionally use compounds described in JP-A No. 157749/1990, page 13, the right lower column, to page 22, the right lower column. By using these compounds, the preservability of the photographic material, the stability of the processing, and the supersensitization effect can be increased uniquely. In particular, it is particularly preferable to additionally use compounds of formulae (VI), (V), and (VI) in the patent. These compounds are used in an amount of $0.5 \times 10^{-5}$ to $5.0 \times 10^{-2}$ mol, preferably $5.0 \times 10^{-5}$ to $5.0 \times 10^{-3}$ mol, per mol of the silver halide, and advantageously the amount to be used is in the range of 0.1 to 10,000 times, preferably 0.5 to 5,000 times, the amount of the sensitizing dye in terms of mols.

As a binding material or a protective colloid that can be used for the photographic material of the present invention, gelatin is advantageously used, but other hydrophilic colloids can be used alone or in combination with gelatin. As a preferable gelatin, a low-calcium gelatin, having a calcium content of 800 ppm or below, more preferably 200 ppm or below, is used. To prevent various mildews and fungi that will propagate in the hydrophilic colloid layer and deteriorate the image, preferably a mildew-proofing agent, such as those described in JP-A No. 271247/1988, is added.

The swelling of the hydrophilic colloid layers comprising the emulsion layers and the nonphotosensitive layers applied on the support of the color photographic material of the present invention in a color developer is required to be rapid in order to attain the objects of the present invention. Specifically, "layer thickness at the time of color development" means the value of the layer thickness at the time when the photographic material is dipped in an aqueous alkali solution at 40° C., and preferably the layer thickness after 30 sec reaches 1.5 times or more the thickness of the dried layer. Preferably the layer thickness reaches 1.5 times or more after 20 sec, more preferably 1.5 times or more after 10 sec. Preferably the layer thickness reaches 5 times or less. The magnification can be easily set, for example, by changing the type of hardener or the amount of the hardener to be added to the hydrophilic colloid layer. Herein the term "thickness of the dried layer" means the value of the layer thickness that is measured when the photographic material is stored for 2 hours or more under conditions of temperature 25° C. and humidity 55%, after which the measurement is carried out under the same conditions. Herein the term "aqueous alkali solution" means an aqueous solution containing 0.2 mol of sodium hydrogencarbonate per liter (the pH is adjusted with sulfuric acid to 10.0).

The photographic material of the present invention may be exposed to visible light or infrared light. The method of exposing it to light may be of exposure to low-illumination-intensity light or high-illumination-intensity light. As a preferable method of exposure high-illumination-intensity light, a laser scanning exposure method can be mentioned, wherein the exposure time per picture element is $10^{-4}$ sec or less, more preferably $10^{-6}$ sec or less. The lower limit of exposure time is not restricted particularly, but it is preferably $10^{-10}$ sec or more.

Further, in the exposure to light, a band strip filter, as described in U.S. Pat. No. 4,880,726, may be preferably used. By using it, light color contamination is eliminated and the color reproduction is remarkably improved.

| Element constituting photographic material | JP-A No. 215272/1987 | JP-A No. 33144/1990 | EP 0,355,660A2 |
|---|---|---|---|
| Silver halide emulsion | p. 10 upper right column 6 to p. 12 lower left column line 5, and p. 12 lower right column 4 from the bottom to p. 13 upper left column line 17 | line p. 28 upper right column line 16 to p. 29 lower right column line 11 and line p. 30 lines 2 to 5 | p. 45 line 53 to p. 47 line 3 and p. 47 lines 20 to 22 |
| Solvent for silver halide | p. 12 lower left column lines 6 to 14 and p. 13 upper left column line 3 from the bottom to p. 18 lower left column last line | — | — |
| Chemical sensitizing agent | p. 12 lower left column line 3 from the bottom to lower right column line 5 from the bottom and p. 18 lower right column line 1 to p. 22 upper right column line 9 from the bottom | p. 29 lower right column line 12 to last line | p. 47 lines 4 to 9 |
| Spectral sensitizing agent (method) | p. 22 upper right column line 8 from the bottom to p. 38 last line | p. 30 upper left column lines 1 to 13 | p. 47 lines 10 to 15 |
| Emulsion stabilizer | p. 39 upper left column line 1 to p. 72 upper right column last line | p. 30 upper left column line 14 to upper right column line 1 | p. 47 lines 16 to 19 |
| Developing accelerator | p. 72 lower left column line 1 to p. 91 upper right column line 3 | — | — |
| Color coupler (Cyan, Magenta, and Yellow coupler) | p. 91 upper right column line 4 to p. 121 upper left column line 6 | p. 3 upper right column line 14 to p. 18 upper left column last line and p. 30 upper right column line 6 to p. 35 lower right column line 11 | p. 4 lines 15 to 27, p. 5 line 30 to p. 28 last line, p. 45 lines 29 to 31 and p. 47 line 23 to p. 63 line 50 |
| Color Formation-strengthen agent | p. 121 upper left column line 7 to p. 125 upper right column line 1 | — | — |
| Ultraviolet absorbing agent | p. 125 upper right column line 2 to p. 127 lower left column last line | p. 37 lower right column line 14 to p. 38 upper left column line 11 | p. 65 lines 22 to 31 |
| Discoloration inhibitor (Image-dye stabilizer) | p. 127 lower right column line 1 to p. 137 lower left column line 8 | p. 36 upper right column line 12 to p. 37 upper left column line 19 | p. 4 line 30 to p. 5 line 23, p. 29 line 1 to p. 45 line 25 p. 45 lines 33 to 40 and p. 65 lines 2 to 21 |
| High-boiling and/or low-boiling solvent | p. 137 lower left column line 9 to p. 144 upper right column last line | p. 35 lower right column line 14 to p. 36 upper left column line 4 from the bottom | p. 64 lines 1 to 51 |
| Method for dispersing additives for photograph | p. 144 lower left column line 1 to p. 146 upper right column line 7 | p. 27 lower right column line 10 to p. 28 upper left column last line and p. 35 lower right column line 12 to p. 36 upper right column line 7 | p. 63 line 51 to p. 64 line 56 |
| Film Hardener | p. 146 upper right column line 8 to p. 155 lower left column line 4 | — | — |
| Developing Agent precursor | p. 155 lower left column line 5 to p. 155 lower right column line 2 | — | — |
| Compound releasing development inhibitor | p. 155 lower right column lines 3 to 9 | — | — |
| Support | p. 155 lower right column line 19 to p. 156 upper left column line 14 | p. 38 upper right column line 18 to p. 39 upper left column line 3 | p. 66 line 29 to p. 67 line 13 |

-continued

| Element constituting photographic material | JP-A No. 215272/1987 | JP-A No. 33144/1990 | EP 0,355,660A2 |
|---|---|---|---|
| Constitution of photosensitive layer | p. 156 upper left column line 15 to p. 156 lower right column line 14 | p. 28 upper right column lines 1 to 15 | p. 45 lines 41 to 52 |
| Dye | p. 156 lower right column line 15 to p. 184 lower right column last line | p. 38 upper left column line 12 to upper right column line 7 | p. 66 lines 18 to 22 |
| Color-mix inhibitor | p. 185 upper left column line 1 to p. 188 lower right coluihn line 3 | p. 36 upper right column lines 8 to 11 | p. 64 line 57 to p. 65 line 1 |
| Gradation controller | p. 188 lower right column lines 4 to 8 | — | — |
| Stain inhibitor | p. 188 lower riqht column line 9 to p. 193 lower right coluihn line 10 | p. 37 upper left column last line to lower right column line 13 | p. 65 line 32 to p. 66 line 17 |
| Surface-active agent | p. 201 lower left column line 1 to p. 210 upper right column last line | p. 18 upper right column line 1 to p. 24 lower right column last line and p. 27 lower left column line 10 from the bottom to lower right column line 9 | — |
| Fluorine-containing agent (As Antistatic gent coatin aid, lubricant, adhesion inhibitor, or the like) | p. 210 lower left column line 1 to p. 222 lower left column line 5 | p. 25 upper left column line 1 to p. 27 lower right coluihn line 9 | — |
| Binder (Hydrophilic colloid) | p. 222 lower left column 6 to p. 225 upper left column last ine | line p. 38 upper right column lines 8 to 18 | p. 66 lines 23 to 28 |
| Thickening agent | p. 225 upper right column line 1 to p. 327 upper right column line 3 | — | — |
| Antistatic agent | p. 227 uyper right column line 3 to p. 230 upper left column line 1 | — | — |
| Polymer latex | p. 230 upper left column line 2 to p. 239 last line | — | — |
| Matting agent | p. 240 upper left column line 1 to p. 240 upper right column last line | — | — |
| Photographic proccessing method (processing process, additive, etc.) | p. 3 upper right column line 7 to p. 10 upper right column line 5 | p. 39 upper left column line 4 to p. 42 upper left column last line | p. 67 line 14 to p. 69 line 28 |

Note: In the cited part of JP-A No. 215272/1987, amendment filed on March 16, 1987 is included. Further, among the above-mentioned couplers, it is preferred to use so called a short wavelength-type yellow coupler, descri ed in JP-A Nos. 231451/1988, 123047/1988, 241547/1988, 173499/1989, 213648/1989, and 250944/1989, as a yellow coupler.

Preferably, the cyan, magenta, and yellow couplers are impregnated into a loadable latex polymer (e.g., as described in U.S. Pat. No. 4,203,716) in the presence (or absence) of a high-boiling organic solvent listed in the above-mentioned table and then the couplers are dissolved in an organic-solvent-soluble polymer, to be emulsified and dispersed in an aqueous hydrophilic colloid solution.

As polymers insoluble in water and soluble in organic solvents that can be preferably used, homopolymers and copolymers described in U.S. Pat. No. 4,857,449, columns 7 to 15, and in International Publication WO 88/00723, pages 12 to 30, can be mentioned. More preferably, use of a methacrylate polymer or an acrylamide polymer is preferred and particularly an acrylamide polymer is preferably used in view, for example, of color image stability.

In the photographic material according to the present invention, color image preservability improving compounds as described in European Patent EP 0277589A2 are preferably used together with couplers, particularly, together with pyrazoloazole couplers and pyrrolotriazole couplers.

That is, the use of a compound (F) described in the above-mentioned patent specifications that combines with the aromatic amine developing agent remaining after the color development processing to form a chemically inactive and substantially colorless compound and/or a compound (G) described in the above-mentioned patent specifications that combines with the oxidized product of the aromatic amine color developing agent remaining after the color development processing to form a chemically inactive and substantially colorless compound simultaneously or singly is preferable. This is because, for example, the occurrence of stain or other side effects due to the formation of color formed dyes by the reaction of the color developing agent or its oxidized product remaining in the film during the storage after the processing with couplers can be prevented.

Further, as the cyan couplers, in addition to diphenylimidazole series cyan couplers described in JP-A No. 33144/1990, 3-hydroxypyridine series cyan couplers described in European Patent EP 0333185A2 (particularly, that formed by attaching a chlorine coupling-off group to the 4-equivalent coupler of Coupler (42) to make it to be 2-equivalent and Couplers (6) and (9) which are listed as specific examples are preferable), cyclic active methylene series cyan couplers described in JP-A No. 32260/1989 (particularly Coupler Examples 3, 8, and 34 that are listed as specific examples are preferable), pyrrolopyrazole series cyan couplers described in European Patent EP 0456226A1, pyrroloimidazole series cyan couplers described in European Patent EP 0484909, and pyrrolotirazole cyan couplers described in European Patents EP 0488248 and EP 491197A1 are preferably used. Among them, pyrrolotriazole cyan couplers are particularly preferably used.

As the yellow couplers, in addition to the compounds listed in the above table, acylacetamide yellow couplers whose acyl group has a 3- to 5-membered cyclic structure described in European Patent EP 0447969A1, malondianilide yellow coupler having a cyclic structure described in European Patent EP 0482552A1, and acylacetamide yellow couplers having a dioxane structure described in U.S. Pat. No. 5,118,599 are preferably used. Among them, acylacetamide yellow couplers whose acyl group is a 1-alkylcyclopropane-1-carbonyl group and malondianilide yellow couplers wherein one of the anilide constitutes an indoline ring are preferably used. These couplers can be used alone or in combination.

As the magenta couplers used in the present invention, 5-pyrazolone series magenta couplers and pyrazoloazole series magenta couplers as described in the known literature shown in the above table are used, but in particular, in view, for example, of the hue, the stability of images, and the color forming properties, pyrazolotriazole couplers wherein a secondary or tertiary alkyl group is bonded directly to the 2-, 3-, or 6-position of the pyrazolotriazole ring as described in JP-A No. 65245/1986, pyrazoloazole couplers containing a sulfonamido group in the molecule as described in JP-A No. 65246/1986, pyrazoloazole couplers having an alkoxyphenylsulfonamido ballasting group as described in JP-A No. 147254/1986, and pyrazoloazole couplers having an alkoxy group or an aryloxy group in the 6-position as described in European Patent Nos. 226,849A and 294,785A are preferably used.

As the processing method of color photographic material of the present invention, besides methods described in the above-described table, processing materials and processing method described in JP-A No. 207250/1990, p.26 (right lower column line 1) to p.34 (right upper column line 9) and in JP-A No. 97355/1992, p.5 (left upper column line 17) to p.18 (right lower column line 20) are preferable.

Color materials and processing methods for use in the present invention will be described in detail. In the present invention, the photographic material is subjected to a color developing, desilvering, and water-washing or stabilizing process. The color developer to be used in the present invention contains known aromatic primary amine color-developing agent. Preferred examples are p-phenylene-diamine derivatives, and as representative examples thereof can be mentioned N,N-diethyl-p-phenylenediamine, 4-amino-N,N-diethyl-3-methylaniline, 4-amino-N-(β-hydroxyethyl)-N-methylaniline, 4-amino-N-ethyl-N-(β-hydroxyethyl)aniline, 4-amino-N-ethyl-N-(β-hydroxyethyl)-3-methylaniline, 4-amino-N-ethyl-N-(3-hydroxypropyl)-3-methylaniline, 4-amino-N-ethyl-N-(4-hydroxybutyl)-3-methylaniline, 4-amino-N-ethyl-N-(β-methanesulfonamidoethyl)-3-methylaniline, 4-amino-N,N-diethyl-3(β-hydroxyethyl)aniline, 4-amino-N-ethyl-N-(β-methoxyethyl)-3-methylaniline, 4-amino-N-(β-ethoxyethyl-N-ethyl-3-methylaniline, 4-amino-N-(3-carbamoylpropyl-N-n-propyl-3-methylaniline, 4-amino-N-(3-carbamoylbutyl-N-n-propyl-3-methylaniline, N-(4-amino-3-methylphenyl)-3-hydroxypyrrolidine, N-(4-amino-3-methylphenyl)-3-(hydroxymethyl)pyrrolidine, and N-(4-amino-3-methylphenyl)-3-pyrrolidinecarboxyamide.

Particularly referable compounds are those represented by the above-described formula (D).

Specific examples are shown below, but the invention is not limited to them.

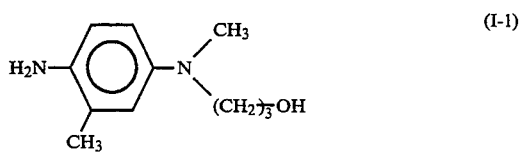

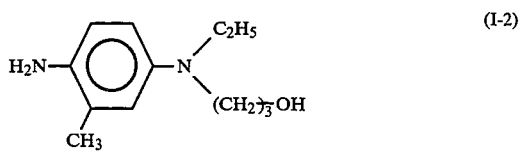

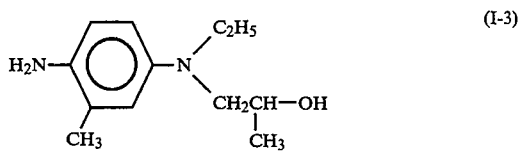

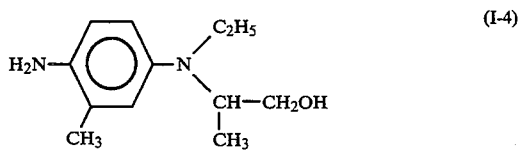

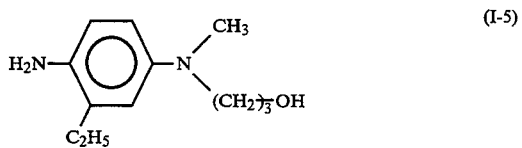

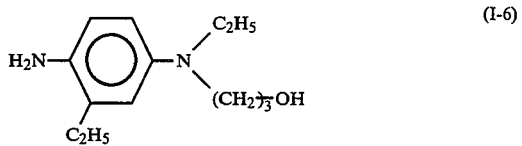

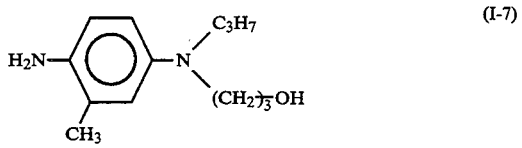

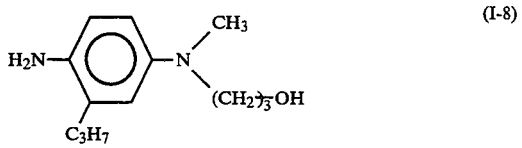

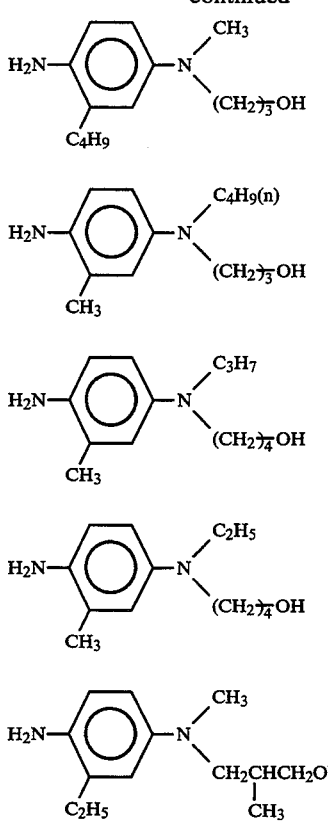

Most preferable compounds are 4-amino-N-ethyl-N-(3-hydroxypropyl)-3-methylaniline and 4-amino-N-ethyl-N-(4-hydroxybutyl)-3-methylaniline.

These p-phenylenediamine derivatives may be in the form of salts such as sulfates, hydrochloride, sulfites, naphtalenedisulfonates, and p-toluenesulfonates. The amount of said aromatic primary amine developing agent to be used is preferably about 0.002 to 0.2 mol, more preferably 0.005 to 0.1 mol, per liter of color developer.

Although the developing time of color developing processing generally adaptable is 45 sec to 3 min, the shorter the better, in view of purpose to achieve rapid processing in the present invention. Concretely, the processing time is preferably 10 to 25 sec. The processing temperature at that time is 20° to 50° C., preferably 30° to 45° C., most preferably 37° to 42° C. Although preferably the replenishing amount is as small as possible, it is suitable that the replenishing amount is 20 to 600 ml, preferably 30 to 200 ml, more preferably 40 to 100 ml, per m² of the photographic material.

In the present invention, "processing time" (e.g., developing time) means the interval from the time of entrance of photographic material to the intended processing solution to the time of its entrance to the solution of succeeding bath.

Further, "the time from the beginning of developing process to the finishing of drying process" means the interval from the entrance to developing bath of developing processing apparatus to going out of the apparatus through the drying process.

In practicing the present invention, preferably the color developer is substantially free from benzyl alcohol. Herein the term "substantially free from benzyl alcohol" means that the concentration of benzyl alcohol is preferably 2 ml/l or below, more preferably 0.5 ml/l or below, and most preferably benzyl alcohol is not contained at all.

It is more preferable that the color developer for use in this invention is substantially free from sulfite ions (herein "substantially free from sulfite ions" means that the concentration of sulfite ions is $3.0 \times 10^{-3}$ mol/l or below), in order to suppress the variation of photographic properties due to the continuous processing and to attain the effects of the invention more remarkably. More preferably the concentration of sulfite ions is $1.0 \times 10^{-3}$ mol/l or below, and most preferably sulfite ion is not contained at all. However, in the present invention, a little amount of sulfite ions contained in a processing agents kit wherein the developing agent has been concentrated before preparing solution to be used, in order to prevent the oxidation of agents, is excluded.

Preferably, the color developer to be used in the present invention is substantially free from sulfite ions, and more preferably, in addition thereto it is substantially free from hydroxylamine (herein "substantially free from hydroxylamine" means that preferably the concentration of hydroxylamine is $5.0 \times 10^{-3}$ mol/l or below), in order to suppress the variation of photographic properties due to the changing of concentration of hydroxylamine. Most preferably hydroxylamine is not contained at all.

It is more preferable that the color developer to be used in the present invention contains an organic preservative instead of above-described hydroxylamine or sulfite ions.

Herein the term "organic preservative" refers to organic compounds that generally, when added to the processing solution for the color photographic material, reduce the speed of deterioration of the aromatic primary amine color-developing agent. That is, organic preservatives include organic compounds having a function to prevent the color developing agent from being oxidized, for example, with air, and in particular, hydroxylamine derivatives (excluding hydroxylamine, hereinafter the same being applied), hydroxamic acids, hydrazines, hydrazides, α-amino acids, phenols, α-hydroxyketones, α-aminoketones, saccharides, monoamines, diamines, polyamines, quaternary ammonium salts, nitroxy radicals, alcohols, oximes, diamide compounds, and condensed cyclic amines are effective organic preservatives. These are disclosed, for example, JP-B No. 30496/1973, JP-A Nos. 143020/1977, 4235/1988, 30845/1988, 21647/1988, 44655/1988, 53551/1988, 43140/1988, 56654/1988, 58346/1988, 43138/1988, 146041/1988, 44657/1988, and 44656/1988, U.S. Pat. Nos. 3,615,503 and 2,494,903, and JP-A Nos. 97953/1989, 186939/1989, 186940/1989, 187557/1989, 306422/1990, and European Patent Publication (OPI) EP0530921A1. As the other preservative, various metals described in JP-A Nos. 44148/1982 and 53749/1982, salicylic acids described in JP-A No. 180588/1984, amines described in JP-A Nos. 239447/1988, 128340/1988, 186939/1989, and 187557/1989, alkanolamines described in JP-A No. 3532/1979, polyethyleneimines described in JP-A No. 94349/1981, aromatic polyhydroxyl compounds described in U.S. Pat. No. 3,746,544 may be included, if needed. It is particularly preferable the addition of alkanolamines, such as triethanolamine, dialkylhydroxylamines, such as N,N-diethylhydroxylamine and N,N-di(sulfoethyl)hydroxylamine, α-amino acid derivatives, such as glysine, alanine, leucine, serine, threonine, valine, isoleucine, or aromatic polyhydroxyl compounds, such as sodium catechol-3,5-disulfonate.

In particular, the use of alkanolamines in combination with dialkylhydroxylamine or the use of dialkylhydroxylamine in combination with α-amino acids, represented by glysine and alkanoleamines, as described in EP Published Patent EP0530921A1, is more preferable in view of stability improvement of the color developer resulting its stability improvement during the continuous processing.

THe amount of these organic preservatives to be added is suitably enough amount to have a function to prevent the deterioration of the color developing agent, and the amount is preferably 0.01 to 1.0 mol/liter, more preferably 0.03 to 0.30 mol/liter.

In the present invention, the color developer preferably contains chlorine ions in an amount of $3.0 \times 10^{-2}$ to $1.5 \times 10^{-1}$ mol/liter, particularly preferably $3.5 \times 10^{-2}$ to $1.0 \times 10^{-1}$ mol/liter. When the concentration of chloride ions is too high, defect such as retarding of development may occur, which is not preferable in view of attaining the object of the present invention, and when the concentration is too low, it is not preferably in view of preventing the fogging.

In the present invention, the color developer preferably contains bromide ions in an amount of $0.5 \times 10^{-5}$ to $1.0 \times 10^{-3}$ mol/l, more preferably $3.0 \times 10^{-5}$ to $5 \times 10^{-4}$ mol/l. When the concentration of bromide ions is too high, developing is retarded, resulting maximum density and sensitivity being lowered, and when the concentration is too low, fogging cannot be prevented sufficiently.

Herein, chloride ions and bromide ions may be added directly to the color developer, or they may be allowed to dissolve out from the photographic material in the color developer at the development processing.

If chloride ions are added directly to the color developer, as the chloride ion-supplying material can be mentioned sodium chloride, potassium chloride, ammonium chloride, lithium chloride, magnesium chloride, and calcium chloride. Further, they may be supplied from a fluorescent brightening agent that is added to the color developer. As the bromide ion-supplying material can be mentioned sodium bromide, potassium bromide, ammonium bromide, lithium bromide, calcium bromide, and magnesium bromide.

When chloride ions and bromide ions are allowed to dissolve out from the photographic material in the color developer, both the chloride ions and bromide ions may be supplied from the emulsion or a source other than the emulsion.

Preferably the pH of the color developer to be used in the present invention is in the range of 9 to 13, more preferably 9 to 12.5, and other known compounds that are components of a conventional developing solution can be contained in the color developer.

In order to keep the above pH, it is preferable to use various buffers. As buffers, use can be made, for example, carbonates, phosphates, borates, tetraborates, hydroxylbenzoates, glycyl salts, N,N-dimathylglycinates, leucinates, norleucinates, guanine salts, 3,4-dihydroxyphenylalanine salts, alanine salts, aminobutyrates, 2-amino- 2-methyl-1,3-propandiol salts, valine salts, proline salts, trishydroxyaminomethane salts, and lysine salts. It is particularly preferable to use carbonates, phosphates, tetraborates, and hydroxybenzoates as buffers, because they have advantages that they are excellent in solubility and in buffering function in the high pH range of a pH 9.0 or higher, they do not adversely affect the photographic function (for example, to cause fogging), and they are inexpensive.

As specified examples of buffer, there are included sodium carbonate, potassium carbonate, sodium bicarbonate, potassium bicarbonate, trisodium phosphate, tripotassium phosphate, disodium phosphate, dipotassium phosphate, sodium borate, potassium borate, sodium tetraborate (borax), potassium tetraborate, sodium o-hydroxybenzoate (sodium salicylate), potassium o-hydroxybenzoate, sodium 5-sulfo-2-hydroxybenzoate (sodium 5-sulfosalicylate), and potassium 5-sulfo-2-hydroxybenzoate (potassium 5-sulfosalicylate).

The amount of buffer to be added to the color developer is preferably 0.1 mol/l or more, and particularly preferably 0.1 to 0.4 mol/l.

Further, to the color developer can be added various chelating agents to prevent calcium or magnesium from precipitating or to improve the stability of the color developer. Specific examples are shown below: nitrilotriacetic acid, diethylenetriaminepentaacetic acid, ethylenediaminetetraacetic acid, N,N,N-trimethylenephosphonic acid, ethylenediamine-N,N,N',N'-tetramethylenephosphonic acid, transcyclohexanediaminetetraacetic acid, 1,2-diaminopropanetetraacetic acid, glycol ether diaminetetraacetic acid, ethylenediamineorthohydroxyphenylacetic acid, 2-phosphonobutane-1,2,4-tricarboxylic acid, 1-hydroxyethylidene-1,1-diphosphonic acid, N,N'-bis(2-hydroxybenzyl)ethylenediamine-N,N'-diacetic acid, hydroxyethyliminodiacetic acid. If necessary, two or more of these chelating agents may be used together.

With respect to the amount of these chelating agents to be added, it is good if the amount is enough to sequester metal ions in the color developer. The amount, for example, is on the order of 0.1 g to 10 g per liter.

If necessary, any development accelerator can be added to the color developer.

As development accelerators, the following can be added as desired: thioether compounds disclosed, for example, in JP-B Nos. 16088/1962, 5987/1962, 7826/1963, 12380/1969, and 9019/1970, and U.S. Pat. No. 3,813,247; p-phenylenediamine compounds disclosed in JP-A Nos. 49829/1977 and 15554/1975; quaternary ammonium salts disclosed, for example, in JP-A No. 137726/1975, JP-B No. 30074/1969, and JP-A Nos. 156826/1981 and 43429/1977; amine compounds disclosed, for example, in U.S. Pat. Nos. 2,494,903, 3,128,182, 4,230,796, and 3,253,919, JP-B No. 11431/1966, and U.S. Pat. Nos. 2,482,546, 2,596,926, and 3,582,346; polyalkylene oxides disclosed, for example, in JP-B Nos. 16088/1962 and 25201/1967, U.S. Pat. No. 3,128,183, JP-B Nos. 11431/1966 and 23883/1967, and U.S. Pat. No. 3,532,501; 1-phenyl-3-pyrazolidones, and imidazoles.

In the present invention, if necessary, any antifoggant can be added. As antifoggants, use can be made of alkali metal halides, such as sodium chloride, potassium bromide, and potassium iodide, and organic antifoggants. As typical organic antifoggants can be mentioned, for example, nitrogen-containing heterocyclic compounds, such as benzotriazole, 6-nitrobenzimidazole, 5-nitroisoindazole, 5-methylbenzotriazole, 5-nitrobenzotriazole, 5-chlorobenzotriazole, 2-thiazolylbenzimidazole, 2-thiazolylmethylbenzimidazole, indazole, hydroxyazaindolizine, and adenine.

The photographic material is generally subjected to a desilvering process after color development. The desilvering process can be carried out by a bleaching process and a fixing process, separately, or carried out at the same time (bleach-fixing process). As the embodiment of desilvering process in the present invention, the bleach-fixing process is preferable for the purpose making steps easy and shortening the processing time. Further, to quicken the process, bleach-fixing may be carried out after the bleaching process. In accordance with the purpose, the process may be arbitrarily carried out using a bleach-fixing bath having two successive tanks, or a fixing process may be carried out before the bleach-fixing process, or a bleaching process may be carried out after the bleach-fixing process.

As the bleaching agent to be used in a bleaching solution and a bleach-fixing solution, use can be made of, for example, iron salts, compounds of polyvalent metals, such as iron (III), cobalt (III), chromium (VI), and copper (II), peracids, quinones, and nitro compounds. As typical bleaching agents, use can be made of iron chlorides, ferricyanides, dichromates, organic complex salts of iron (III) (e.g., complex salts of aminopolycarboxylic acid, such as ethylenediaminetetraacetic acid, diethylenetriaminepentaacetic acid, cyclohexanediaminetetraacetic acid, methyliminodiacetic acid, 1,3-diaminopropanetetraacetic acid, and glycoletherdiaminetetraacetic acid), persulfates, bromates, permanganates, and nitrobenzenes. Of these, aminopolycarboxylic acid complex salts of iron (III), including ethylenediaminetetraacetic acid iron (III) complex salts and 1,3-diaminopropanetetraacetic acid iron (III) complex salts are preferable in view of the rapid processing and the prevention of environmental pollution. Further, aminopolycarboxylic acid iron (III) complex salts are particularly useful in a bleaching solution as well as a bleach-fix solution. The bleaching solution or the bleach-fix solution using these aminopolycarboxylic acid iron (III) complex salts is generally used in pH 3 to 8.

Known additives, for example, a rehalogenating agent such as ammonium bromide and ammonium chloride, a pH buffer such as ammonium nitrare, and a metal-corrosion-preventing agent such as ammonium sulfate can be added in the bleaching solution or the bleach-fix solution.

In addition to the above-described compounds, an organic acid is preferably contained in the bleaching solution and the bleach-fix solution. Particularly preferable organic acids include compounds having an acid dissociation constant (pKa) of 2 to 5.5, and specifically acetic acid and propionic acid are preferable.

Although as the fixing agents to be used in the fixing solution and bleach-fix solution use can be made of thiosulfates, thiocyanates, thioether compounds, thioureas, and a large amount of iodide salts, the use of thiosulfate is general, particularly ammonium thiosulfate can be used most widely. Further, combination use of thiosulfate with thiocyanate, thioether compound, or thiourea is also preferable.

As a preservative for the fixing solution and the bleach-fixing solution, sulfites, bisulfites, carbonyl-bisulfic acid adduct or sulfinic acid compounds described in European Patent No. 294769A are preferable. Further, it is preferable to add various aminopolycarboxylic acids or organic phosphonic acids (e.g., 1-hydroxyethylidene-1,1-diphosphonic acid and N,N,N',N'-ethylenediaminetetraphosphonic acid) in the fixing solution and the bleach-fix solution for the purpose to stabilize the solution.

Further, in the fixing solution and the bleach-fixing solution, various fluorescent brightening agents, antifoamers, surface-active agents, poly(vinyl pyrrolidone), and methanol can be included.

In the bleaching solution, the bleach-fix solution, and/or bath preceding them, various compounds may be used as a bleach-accelerating agent, according to a need. As specific examples of useful bleach-accelerating agents, use can be made of, for example, compounds having a mercapto group or a disulfido group, described in U.S. Pat. No. 3,893,858, West German Patent No. 1,290,812, and JP-A No. 95630/1978, and *Research Disclosure* No. 17129 (July 1978), thiazolizine compounds described in JP-A No. 140129/1975, thiourea compounds described in U.S. Pat. No. 3,706,561, iodide salts described in JP-A No. 16235/1983, polyoxyethylene compounds described in West German Patent No. 2,748,430, polyamine compounds described in JP-B No. 8836/70, and bromide ions. Among them, compounds having a mercapto group or disulfide group are preferable in view of large accelerating effect, in particular, compounds described in U.S. Pat. No. 3,893,858, West German Patent No. 1,290,812, and JP-A No. 95630/1978 are preferable. Further, the compound described in U.S. Pat. No. 4,552,834 is also preferable. These bleach-accelerating agents may be added in the photographic material.

The shorter the total time of the bleaching and fixing steps is, the more preferable it is within the range wherein silver retention does not occur in view of the object of shortening of processing time. Preferably it is 5 sec to 1 min, more preferably 5 sec to 25 sec. The processing temperature is in a range of from 25° to 50° C., preferably 35° to 45° C. In the preferable temperature range, the desilvering speed is improved and occurrence of stain after the processing is effectively prevented.

In the processing step of the present invention, although any known method for stirring can be applied for processing process in the present invention, preferably the stirring is enhanced as much as possible. Specific techniques for enhancing the stirring that can be mentioned include a method described in JP-A No. 183460/1987 or No. 183461/1987, wherein a jet of a processing liquid is caused to impinge upon the emulsion surface of a photographic material; a method described in JP-A No. 183461/1987, wherein a rotating means is used for increasing the stirring effect; a method wherein a photographic material is moved with a wiper blade provided in a liquid in contact with the emulsion surface, to make the liquid near the emulsion surface turbulent, thereby improving the stirring effect; and a method wherein the circulated flow rate of all the processing liquid is increased. Such a means of improving stirring is effective for any of a developer, a bleaching solution, a bleach-fix solution, a fixing solution, an washing and/or a stabilizing solution.

In each of the above-described processing solutions adaptable in the present invention, a method for jetting out a solution pressurized and forwarded by pump through a slit or a nozzle provided against to the emulsion surface, as described in JP-A No. 183460/1987 (in Examples from page 3 right lower column to page 4 right lower column), can be applied.

The processing of the present invention exhibits an excellent performance compared with combination methods other than the present invention at any state of opened surface ratio of processing solution [(Contact surface area (cm$^2$) of the processing solution with the air)/(Whole volume (cm$^3$) of the processing solution)]. However, the opened surface ratio is preferably 0 to 0.1 cm$^{-1}$, in view of the stability of solution constituents. In the continuous processing, for a practical use, the opened surface ratio is preferably in the range from 0.001 to 0.05 cm$^{-1}$, more preferably in the range from 0.002 to 0.03 cm$^{-1}$.

Generally, the color photographic material of the present invention is subjected to a washing step after the desilvering process. Instead of the washing step, a stabilizing step can be carried out. In such a stabilizing process, any of known methods described in JP-A Nos. 8543/1982, 14834/1983, and 220345/1985 can be used. A washing step/stabilizing step, wherein a stabilizing bath containing a dye stabilizer and a surface-active agent that is typically used for processing a photographing color photographic material is used as a final bath, can be carried out.

The washing solution and the stabilizing solution can contain a water softener, such as an inorganic phosphoric acid, polyaminocarbonic acid and an organic aminophosphonic acid; a metal salt such as an Mg salt, an Al salt, and a Bi salt; a surface-active agent; and a hardening agent.

The amount of washing water in the washing step can be set over a wide range, depending on the characteristics of the photographic material (e.g., the characteristics of the material used, such as couplers), the usage of the photographic material, the washing water temperature, the number of the washing water tanks (stages), the type of replenishing, such as the countercurrent type or of the down flow type, and other various conditions. Further, to solve such problems as the propagation of bacteria when the amount of washing water is decreased greatly at a countercurrent flow system and the adhering of suspended matter to the photographic material, the method for reducing calcium ions and magnesium ions, described in JP-A No. 288838, can be used quite effectively. Also, isothiazolone compounds and cyabendazoles described in JP-A No. 8542/1982, chlorine-type disinfectant such as chlorinated sodium isocyanurate, benzotriazoles, and other bactericides described by Hiroshi Horiguchi in *Bokin Bobai-zai no Kagaku*, (1986) published by Sankyo-Shuppan, *Bisei-butsu no Mekkin, Sakkin, Bobaigijutsu* (1982) edited by Eiseigijutsu-kai, published by Kogyo-Gijutsu-kai, and in *Bokin Bobaizai Jiten* (1986) edited by Nihon Bokin Bobai-gakkai, can be used.

The pH of the washing water used in the washing step is 4 to 9, preferably 5 to 8. The washing water temperature and the washing time to be set may vary depending, for example, on the characteristics and the application of the photographic material, and they are generally selected in the range of 15° to 45° C. for 10 sec to 5 min, and preferably in the range of 25° to 40° C. for 15 sec to 2 min.

As dye-stabilizing agents to be able to use in a stabilizing solution, aldehydes such as formalin and gultalaldehyde, N-methylol compounds, hexamethylenetetramine, and aldehyde-sulfic acid adduct can be mentioned. Further, the stabilizing solution can contain pH controlling buffer, such as boric acid and sodium hydride, 1-hydroxyethylidene-1,1-diphosphonic acid, chelating agent, such as ethylenediaminetetraacetic acid, sulfulation-preventer, such as alkanolamine, fluorescent brightening agent, and antimold agent.

The over-flowed solution due to the above-mentioned replenishing of washing solution and/or stabilizing solution may be reused in other steps, such as a desilvering step.

In the processing using an automatic processor, it is preferable to correct the concentration of processing solution by adding water when concentration due to evaporation occurs.

In the present invention, an washing water and/or a stabilizing water treated by a reverse osmosis membrane can be used effectively. As the raw material of the reverse osmosis membrane, cellulose acetate, crosslinked polyamide, polyether, polysulfone, polyacrylic acid, polyvinylenecarbonate, or the like can be used.

The feeding pressure of solution for these membrane is preferably 2 to 10 kg/cm$^2$, more preferably 3 to 7 kg/cm$^2$ in view of preventing stain and decrease of amount of permeated solution.

The water-washing process and/or stabilizing process are preferably carried out in a multistage-countercurrent mode using multiple tanks, particularly preferably using 2 to 5 tanks.

The treatment by a reverse osmosis membrane is preferably conducted to the water after the second tank in said multistage countercurrent washing process and/or stabilizing process. Concretely, water in the second tank in a 2-tanks constitution, water in the second or third tank in a 3-tanks constitution, or water in the third or fourth tank in a 4-tanks constitution is treated by a reverse osmosis membrane, and the water permeated is returned to the same tank (from which tank water to be treated was withdrawn) or a tank afterward positioned in the washing and/or stabilizing process. Further, in one response to the reverse osmosis treatment, the concentrated washing solution and/or stabilizing solution are fed back to the preceding bleach-fix bath.

The silver halide color photographic material of the present invention may contain therein a color-developing agent for the purpose of simplifying and quickening the process. To contain such a color-developing agent, it is preferable to use a precursor for color-developing agent. For example, indoaniline-series compounds described in U.S. Pat. No. 3,342,597, Schiff base-type compounds described in U.S. Pat. No. 3,342,599 and *Research Disclosure* Nos. 14850 and 15159, aldol compounds described in *Research Disclosure* No. 13924, and metal salt complexes described in U.S. Pat. No. 3,719,492, and urethane-series compounds described in JP-A No. 135628/1978 can be mentioned.

For the purpose of accelerating the color development, the silver halide color photographic material of the present invention may contain, if necessary, various 1-phenyl-3-pyrazolidones. Typical compounds are described in JP-A Nos. 64339/1981, 144547/1982, and 115438/1983.

The diaminostilbene series compounds according to the present invention can be used as a fluorescent whitening agent for photography, a whitening agent for fiber, and the like.

According to the method of the present invention, a method for forming an image, that fluorescent whitening agents in a processing solution do not crystallize in a development processing of a silver halide photographic material and processed photographic-material have little residual color, can be provided.

Next, the present invention will be described in detail in accordance with examples, but the invention is not limited to them.

EXAMPLE 1

Preparation of Photographic Material

A multilayer color printing paper having layer compositions shown below was prepared by coating various photographic constituting layers on a paper support laminated on both sides thereof with polyethylene film, followed by subjecting to a corona discharge treatment on the surface thereof and provided a gelatin undercoat layer containing sodium dodecylbenzene sulfonate. Coating solutions were prepared as follows:

Preparation of the First Layer Coating Solution 153.0 Grams of yellow coupler (ExY), 15.0 g of image-dye stabilizer (Cpd-1), 7.5 g of image-dye stabilizer (Cpd-2), 16.0 g of image-dye stabilizer (Cpd-3) were dissolved in 25 g of solvent (Solv-1), 25 g of solvent (Solv-2), and 180 ml of ethyl acetate, and the resulting solution was dispersed and emulsified in 1,000 ml of 10% aqueous gelatin solution containing 60 ml of 10% sodium dodecylbenzene sulfonate solution and 10 g of citric acid, thereby prepared emulsified dispersion A. Separately silver chlorobromide emulsion A (cubic grains, 3:7 (silver mol ratio) blend of large size emulsion A having 0.88 μm of average grain size and small size emulsion A having 0.70 μm of average grain size, and 0.08 and 0.10 of deviation coefficient of grain size distribution, respectively, each in which 0.3 mol % of silver bromide was located at a part of grain surface, the balance was silver chloride) was prepared. Blue-sensitive sensitizing dyes A and B, shown below, were added in amounts of dyes that corresponds to $2.0 \times 10^{-4}$ mol and $2.5 \times 10^{-4}$ mol to the large size emulsion A and small size emulsion A, per mol of silver, respectively. The chemical sensitizing of this emulsion was carried out by adding sulfur sensitizing agent and gold sensitizing agent.

The above-described emulsified dispersion A and this silver chlorobromide emulsion A were mixed together and dissolved to give the composition shown below, thereby preparing the first layer coating solution.

Preparation of Coating Solutions for the Second to Seventh Layers

Coating solutions for the second to seventh layers were also prepared in the same manner as the coating solution of first layer.

Photographic material Sample having layer composition shown below were prepared by coating the above-described each layer coating solution on a support.

As a gelatin hardener for the respective layers, 1-oxy-3,5-dichloro-s-triazine sodium salt was used.

Further, Cpd-14 and Cpd-15 were added in each layer in such amounts that the respective total amount becomes 25.0 mg/m² and 50.0 mg/m².

Spectral sensitizing dyes shown below were used in respective silver chlorobromide emulsions of photosensitive emulsion layers.

Blue-sensitive emulsion layer:

Sensitizing dye A

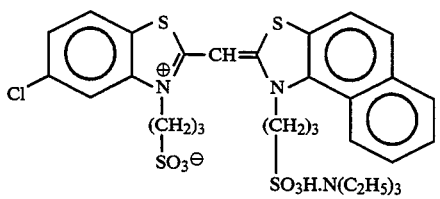

and

Sensitizing dye B

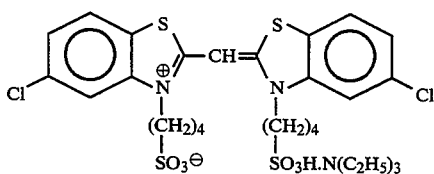

(each $2.0 \times 10^{-4}$ mol to the large size emulsion and $2.5 \times 10^{-4}$ mol to the small size emulsion, per mol of silver halide.)

Green-sensitive emulsion layer:

Sensitizing dye C

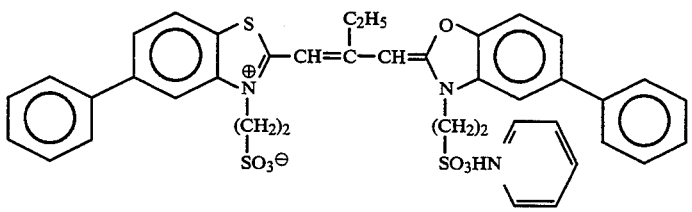

($4.0 \times 10^{-4}$ mol to the large size emulsion and $5.6 \times 10^{-4}$ mol to the small size emulsion, per mol of silver halide) and Sensitizing dye D

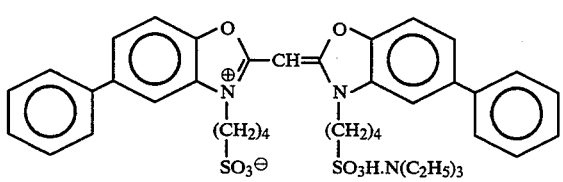

($7.0 \times 10^{-5}$ mol to the large size emulsion and $1.0 \times 10^{-5}$ mol to the small size emulsion, per mol of silver halide)

Red-sensitive emulsion layer:

Sensitizing dye E

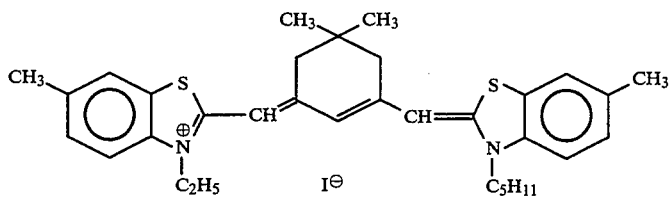

(0.9×10$^{-4}$ mol to the large size emulsion and 1.1×10$^{-4}$ mol to the small size emulsion, per mol of silver halide)

To the red-sensitive emulsion layer, the following compound was added in an amount of 2.6×10$^{-3}$ mol per mol of silver halide:

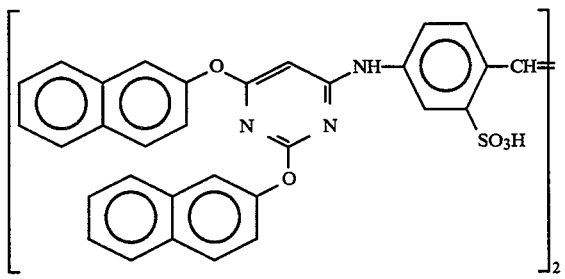

Further, 1-(5-methylureidophenyl)-5-mercaptotetrazole was added to the blue-sensitive emulsion layer, the green-sensitive emulsion layer, and the red-sensitive emulsion layer in amount of 8.5×10$^{-5}$ mol, 7.7×10$^{-4}$ mol, and 2.5×10$^{-4}$ mol, per mol of silver halide, respectively.

Further, 4-hydroxy-6-methyl-1,3,3a,7-tetrazaindene was added to the blue-sensitive emulsion layer and the green-sensitive emulsion layer in amount of 1×10$^{-4}$ mol and 2×10$^{-4}$ mol, per mol of silver halide, respectively.

The dyes shown below (figure in parentheses represents coating amount) were added to the emulsion layers for prevention of irradiation.

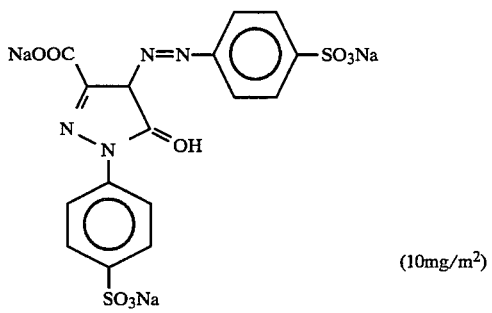

(Dye-1)

(10mg/m$^2$)

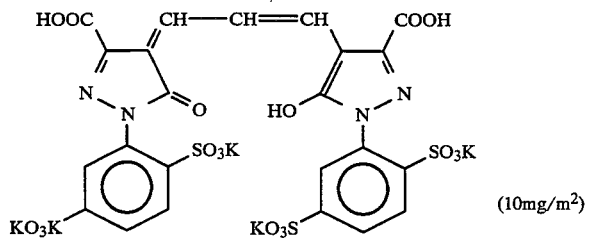

(Dye-2)

(10mg/m$^2$)

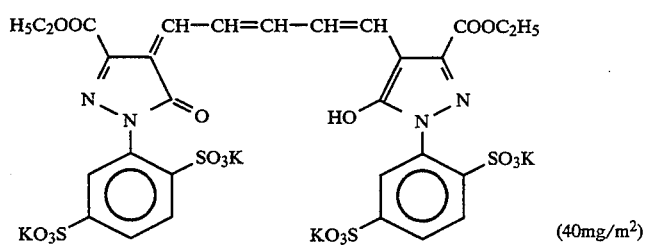

(Dye-3)

(40mg/m$^2$)

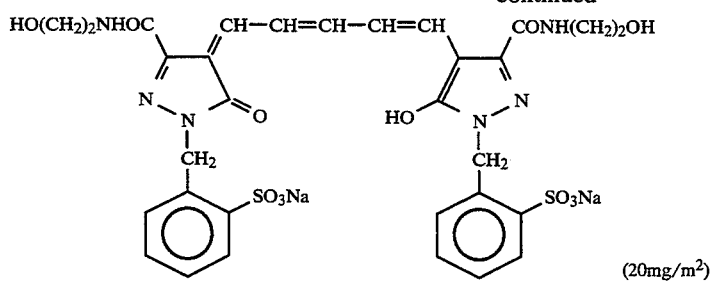

(Dye-4)

(20mg/m²)

Composition of Layers

The composition of each layer is shown below. The figures represent coating amount (g/m²). The coating amount of each silver halide emulsion is given in terms of silver.

Supporting Base
Paper laminated polyethylene
[a white pigment (TiO₂) and a bluish dye (ultramarine) were included in the first layer side of the polyethylene-laminated film]

| First Layer (Blue-sensitive emulsion layer) | |
|---|---|
| The above described silver chlorobromide emulsion A | 0.27 |
| Gelatin | 1.36 |
| Yellow coupler (ExY) | 0.79 |
| Image-dye stabilizer (Cpd-1) | 0.08 |
| Image-dye stabilizer (Cpd-2) | 0.04 |
| Image dye stabilizer (Cpd-3) | 0.08 |
| Solvent (Solv-1) | 0.13 |
| Solvent (Solv-2) | 0.13 |
| Second Layer (Color-mix preventing layer) | |
| Gelatin | 1.00 |
| Color mix inhibitor (Cpd-4) | 0.06 |
| Solvent (Solv-7) | 0.03 |
| Solvent (Solv-2) | 0.25 |
| Solvent (Solv-3) | 0.25 |
| Third Layer (Green-sensitive emulsion layer) | |
| Silver chlorobromide emulsion B (cubic grains, 1:3 (Ag molar ratio) blend of large size emulsion B having average grain size of 0.55 μm and small size emulsion B having average grain size of 0.39 μm, whose deviation coefficient of grain size distribution are 0.10 and 0.08, respectively, each in which emulsion 0.8 mol % of AgBr was located at a part of grain surface, the balance was AgCl) | 0.13 |
| Gelatin | 1.45 |
| Magenta coupler (ExM) | 0.16 |
| Image-dye stabilizer (Cpd-5) | 0.15 |
| Image-dye stabilizer (Cpd-2) | 0.03 |
| Image-dye stabilizer (Cpd-6) | 0.01 |
| Image-dye stabilizer (Cpd-7) | 0.01 |
| Image-dye stabilizer (Cpd-8) | 0.08 |
| Solvent (Solv-3) | 0.50 |
| Solvent (Solv-4) | 0.15 |
| Solvent (Solv-5) | 0.15 |
| Fourth Layer (Color-mix preventing layer) | |
| Gelatin | 0.70 |
| Color-mix inhibitor (Cpd-4) | 0.04 |
| Solvent (Solv-7) | 0.02 |
| Solvent (Solv-2) | 0.18 |
| Solvent (Solv-3) | 0.18 |
| Fifth Layer (Red-sensitive emulsion layer) | |
| Silver chlorobromide emulsion C (cubic grains, 1:4 (Ag molar ratio) blend of large size emulsion C having average grain size of 0.50 μm and small size emulsion C having average grain size of 0.41 μm, whose deviation coefficient of grain size distribution are 0.09 and 0.11, respectively, each in which emulsion 0.8 mol % of AgBr was located at a part of grain surface, the balance was AgCl) | 0.18 |
| Gelatin | 0.80 |
| Cyan coupler (ExC) | 0.33 |
| Image-dye stabilizer (Cpd-1) | 0.35 |
| Ultraviolet absorber (UV-2) | 0.18 |
| Image-dye stabilizer (Cpd-9) | 0.15 |
| Image-dye stabilizer (Cpd-10) | 0.15 |
| Image-dye stabilizer (Cpd-11) | 0.01 |
| Solvent (Solv-6) | 0.22 |
| Image-dye stabilizer (Cpd-8) | 0.01 |
| Image-dye stabilizer (Cpd-6) | 0.01 |
| Solvent (Solv-1) | 0.01 |
| Sixth Layer (Ultraviolet absorbing layer) | |
| Gelatin | 0.55 |

-continued

| | |
|---|---|
| Ultraviolet absorber (UV-1) | 0.38 |
| Image-dye stabilizer (Cpd-12) | 0.15 |
| Image-dye stabilizer (Cpd-5) | 0.02 |
| Seventh Layer (Protective layer) | |
| Gelatin | 1.13 |
| Acryl-modified copolymer of polyvinyl alcohol (modification degree: 17%) | 0.05 |
| Liquid paraffin | 0.02 |
| Image-dye stabilizer (Cpd-13) | 0.01 |

(ExY) Yellow coupler

Mixture ((a):(b) = 1:1 in molar ratio) of (a) R = 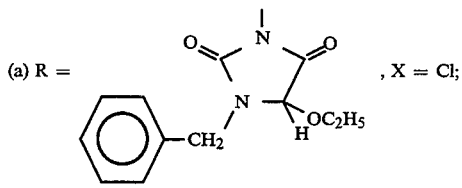 , X = Cl;

(b) R = 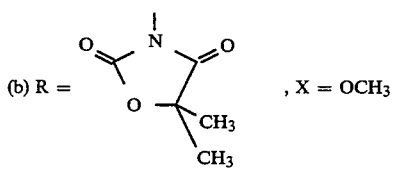 , X = OCH$_3$ of the following formula

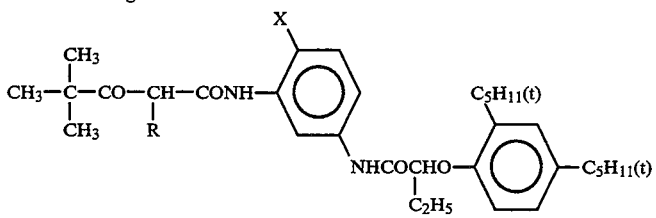

(ExM) Magenta coupler

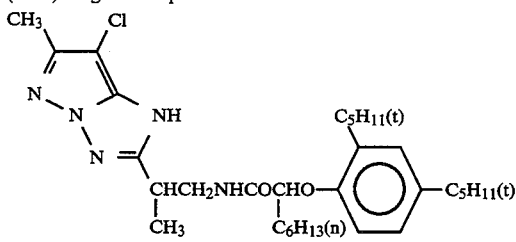

(ExC) Cyan coupler

Mixture (3:7 in molar ratio) of

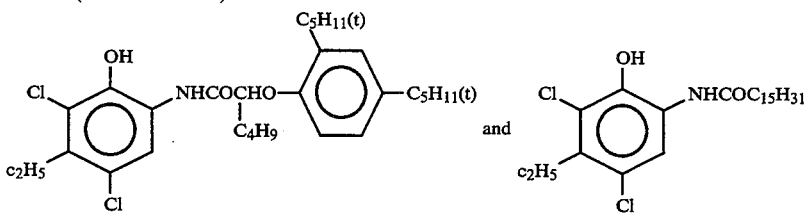

(Cpd-1) Image-dye stabilizer

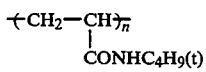

Av. molecular weight: 60,000

(Cpd-2) Image-dye stabilizer

-continued
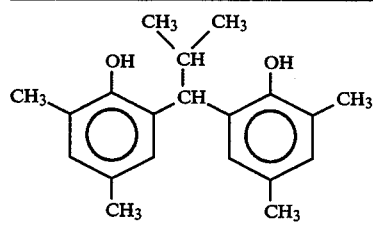
(Cpd-3) Image-dye stabilizer
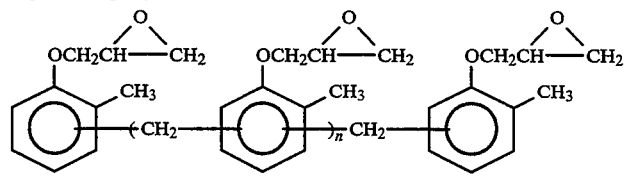
n = 7–8 (in average)
(Cpd-4) Color-mix inhibitor
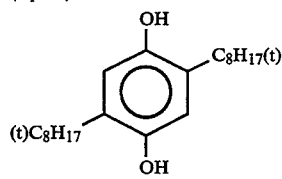
(Cpd-5) Image-dye stabilizer
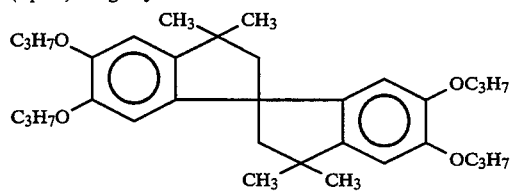
(Cpd-6) Image-dye stabilizer
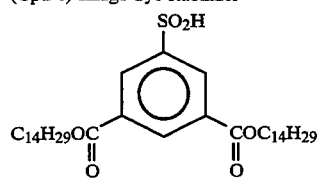
(Cpd-7) Image-dye stabilizer
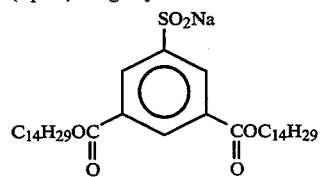
(Cpd-8) Image-dye stabilizer
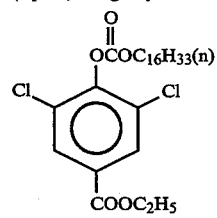
(Cpd-9) Image-dye stabilizer

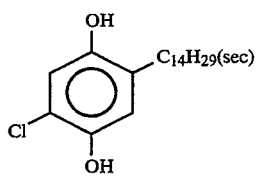
(Cpd-10) Image-dye stabilizer
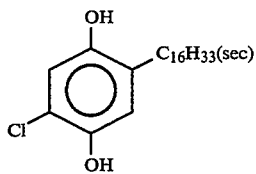
(Cpd-11) Image-dye stabilizer
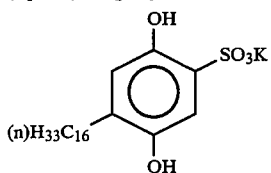
(Cpd-12) Image-dye stabilizer
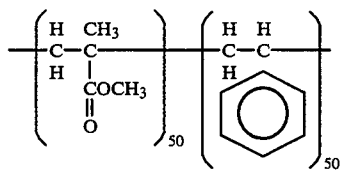
Av. molecular weight: 60,000
(Cpd-13) Image-dye stabilizer
$$C_{13}H_{27}CONH(CH_2)_3\overset{\overset{CH_3}{\oplus}}{\underset{CH_3}{N}}CH_2COO^{\ominus}$$
(Cpd-14) Antiseptic
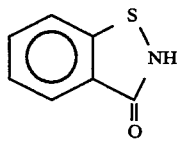
(Cpd-15) Antiseptic
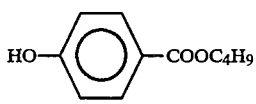
(UV-1) Ultraviolet ray absorber
Mixture of (i), (ii), (iii), and (iv) (10:5:1:5 in weight ratio)
(i) 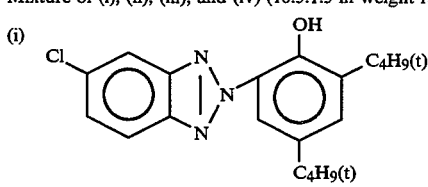, (ii) 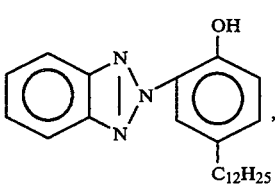, (iii) 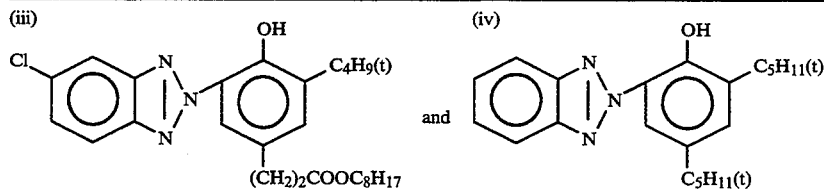 (iv)
(UV-2) Ultraviolet ray absorber
mixture of (1), (2), and (3) (1:2:2 in weight ratio)
(1) 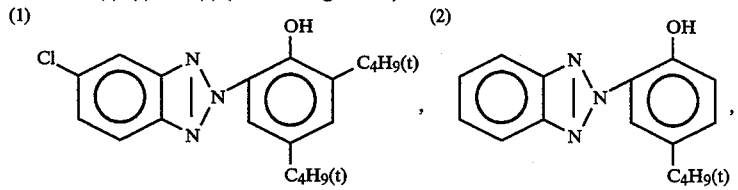 (2)
and
(3) 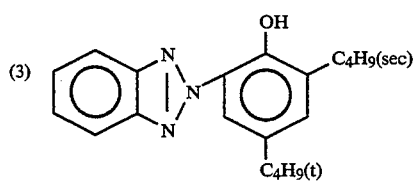
(Solv-1) Solvent
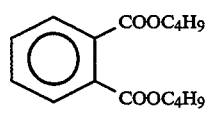
(Solv-2) Solvent
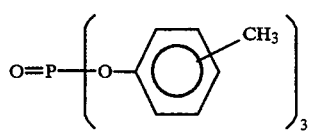
(Solv-3) Solvent
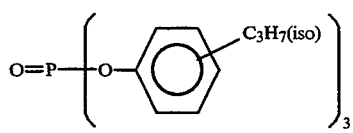
(Solv-4) Solvent
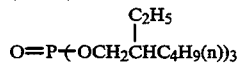
(Solv-5) Solvent
$$O=P(OCH_2\overset{C_2H_5}{\underset{|}{C}}HC_4H_9(n))_3$$
(Solv-6) Solvent
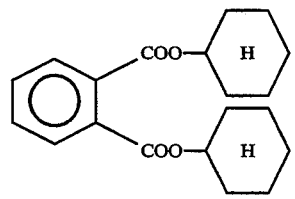
(Solv-7) Solvent

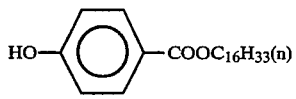

Processing Process 1

A continuous processing (running test) of above prepared photographic printing paper was conducted, after exposure to light, according to the processing process shown below and using respective color developers (101) to (105), until the replenishing rate reached to the tank volume of the developer.

| Processing step | Temperature | Time | Replenisher* | Tank Volume |
|---|---|---|---|---|
| Color developing | 40° C. | 25 sec | 73 ml | 2 liter |
| Bleach-fixing | 40° C. | 25 sec | 60 ml** | 2 liter |
| Rinse (1) | 35–40° C. | 15 sec | — | 1 liter |
| Rinse (2) | 35–40° C. | 15 sec | — | 1 liter |
| Rinse (3) | 35–40° C. | 15 sec | 360 ml | 1 liter |
| Drying | 80° C. | 20 sec | | |

| Color-developer (101) | Tank solution | Replenisher |
|---|---|---|
| Water | 700 ml | 700 ml |
| Sodium triisopropylnaphthalene-($\beta$) sulfonate | 0.1 g | 0.1 g |
| Ethylenediaminetetraacetic acid | 3.0 g | 3.0 g |
| Disodium 1,2-dihydroxybenzene-4,6-disulfonate | 0.5 g | 0.5 g |
| Triethanolamine | 12.0 g | 12.0 g |
| Potassium chloride | 6.5 g | — |
| Potassium bromide | 0.03 g | — |
| Potassium carbonate | 27.0 g | 27.0 g |
| Sodium sulfite | 0.1 g | 0.1 g |
| Disodium-N,N-bis(sulfonatoethyl)-hydroxylamine | 10.0 g | 13.0 g |
| N-Ethyl-N-($\beta$-methanesulfonamido-ethyl)-3-methyl-4-aminoaniline sulfate | 7.0 g | 15.0 g |
| Water to make | 1,000 ml | 1,000 ml |
| pH (25° C.) | 10.35 | 11.6 |

Note:
*Replenisher amount per $m^2$ of photographic material.
**In addition to the above 60 ml, 120 ml/$m^2$ of photographic material was let flow from the tank of rinse (1).
Rinsing steps were carried out in 3-tanks countercurrent mode from the tank of rinse (3) toward the tank of rinse (1).

Color developers (102), (103), (104), and (105) were prepared by adding respective fluorescent whitening agents shown below to color developer (101).

| Color developer | Fluorescent whitening agent | Added amount (g/liter) | |
|---|---|---|---|
| (102) | (B-1) | 2.0 | (Tank solution) |
| | " | 4.0 | (Replenisher) |
| (103) | (B-4) | 2.0 | (Tank solution) |
| | " | 4.0 | (Replenisher) |
| (104) | (SR-13) | 2.0 | (Tank solution) |
| | " | 4.0 | (Replenisher) |
| (105) | (SR-25) | 2.0 | (Tank solution) |
| | " | 4.0 | (Replenisher) |

The pH of each developer was adjusted to the same pH of tank solution or replenisher of color developer (101).

| Bleach-fix solution | Tank Solution | Replenisher |
|---|---|---|
| Water | 600 ml | 150 ml |
| Ammonium thiosulfate (700 g/l) | 100 ml | 250 ml |
| Ammonium sulfite | 10 g | 20 g |
| Iron (III) ammonium ethylenediaminetetraacetate | 77 g | 150 g |
| Ethylenediaminetetraacetic acid | 5 g | 12.5 g |
| Ammonium bromide | 40 g | 75 g |
| Nitric acid (67%) | 30 g | 65 g |
| Water to make | 1,000 ml | 1,000 ml |
| pH (25° C.) | 5.8 | 5.6 |

(pH was adjusted by acetic acid or aqueous ammonia)

Rinse Solution

Ion-exchanged water (Calcium and Magnesium each are 3 ppm or below).

Processing Process 2

A continuous processing was conducted in the same manner as the above processing process 1, except that rinse processes were changed as follows, to be made easy and rapid.

| Processing step | Temperature | Time | Replenisher* | Tank Volume |
|---|---|---|---|---|
| Color developing | 40° C. | 25 sec | 73 ml | 2 liter |
| Bleach-fixing | 40° C. | 25 sec | 60 ml | 2 liter |
| Rinse (1) | 40° C. | 3 sec | — | 1 liter |
| Rinse (2) | 40° C. | 3 sec | — | 1 liter |
| Rinse (3) | 40° C. | 3 sec | — | 1 liter |
| Rinse (4) | 40° C. | 3 sec | — | 1 liter |
| Rinse (5) | 40° C. | 6 sec | 90 ml | 1 liter |
| Drying | 80° C. | 20 sec | | |

Note:
*Replenisher amount per $m^2$ of photographic material.
Rinsing steps were carried out in 5-tanks countercurrent mode from the tank of rinse (5) toward the tank of rinse (1).

In the above processing, water from rinse (5) was pressurized and fed to reverse osmosis membrane, and the permeated water was fed to rinse (5), while the concentrated water which had not permeated through the membrane was returned to rinse (4) and reused. Further, in order to shorten the crossover time between respective rinse processes there were provided with blades between tanks of rinse through which the photographic material passed.

As compositions of processing solutions used in processing process 2, those of the above-described color developers (101) to (105) and bleach-fix solution were used.

After continuous processing according to the above processing processes 1 and 2 were completed, gradation-exposed color printing paper was processed using each processing solution. The processed each sample was determined yellow reflective density by a reflection characteristics curve, and the minimum density was determined.

Further, an unexposed color printing paper was processed, and the residual color was determined by the following procedure.

Determination of Residual Color

The sensitizing dye remaining on processed color printing paper was extracted by methanol/water (1/1), and the amount was determined by a high-performance liquid chromatography analysis. Results are shown in Table 1 in terms of residual ratio (100×residual amount/coating amount, %) of each sensitizing dye A and B.

Separately, each 100 ml of replenisher of the above color developers (101) to (105) was introduced in a bottle made of poly(vinyl chloride), and the bottle was sealed hermetically and stored at 5° C. for 5 days. Then the precipitate in the bottle was observed to carry out a crystallization test.

Results are shown in Table 1.

TABLE 1

| Color Developer No. | Fluorescent Whitening Agent No. | Residual Color Test | | | Crystallization Test (5° C., 5 Days) | Remarks |
|---|---|---|---|---|---|---|
| | | Residual Rate (%) Sensitizing Dye | | Dmin (Yellow) | | |
| | | A | B | | | |
| Processing Process 1 | | | | | | |
| (101) | — | 62 | 64 | 0.14 | — | Comparative Example |
| (102) | (B-1) | 40 | 42 | 0.11 | Precipitates | " |
| (103) | (B-4) | 45 | 45 | 0.12 | " | " |
| (104) | (SR-13) | 25 | 28 | 0.08 | No Precipitate | This Invention |
| (105) | (SR-25) | 27 | 30 | 0.08 | " | " |
| Processing Process 2 | | | | | | |
| (101) | — | 70 | 71 | 0.16 | — | Comparative Example |
| (102) | (B-1) | 55 | 59 | 0.13 | Precipitates | " |
| (103) | (B-4) | 58 | 58 | 0.14 | " | " |
| (104) | (SR-13) | 33 | 35 | 0.09 | No Precipitate | This Invention |
| (105) | (SR-25) | 37 | 39 | 0.10 | " | " |

Note: Altanated points of Process 1 from Proces 2:
Replenishing rate of rinsing steps 360 ml/m² → 90 ml/m²
Processing time of rinsing steps 45 sec → 18 sec As is apparent from the results in Table 1, the development processing solution according to the present invention does not bring out deposition during the storage at a low temperature, and a white background less in residual color after processing by the color developer according to the present invention can be provided.

EXAMPLE 2

Processing process 3

A continuous processing (running test) of above prepared photographic printing paper was conducted, after exposure to light, according to the processing process shown below and using respective color developers (201) to (205), until the replenishing rate reached to the tank volume of the developer.

| Processing step | Temperature | Time | Replenisher* | Tank Volume |
|---|---|---|---|---|
| Color developing | 40° C. | 15 sec | 35 ml | 2 liter |
| Bleach-fixing | 40° C. | 15 sec | 35 ml | 2 liter |
| Rinse (1) | 40° C. | 3 sec | — | 1 liter |
| Rinse (2) | 40° C. | 3 sec | — | 1 liter |
| Rinse (3) | 40° C. | 3 sec | — | 1 liter |
| Rinse (4) | 40° C. | 3 sec | — | 1 liter |
| Rinse (5) | 40° C. | 6 sec | 60 ml | 1 liter |
| Drying | 80° C. | 20 sec | | |

Note:
Replenisher amount per m² of photographic material.
Rinsing steps were carried out in 5-tanks countercurrent mode from the tank of rinse (5) toward the tank of rinse (1).

In the above processing, water from rinse (5) was pressurized and fed to reverse osmosis membrane, and the permeated water was fed to rinse (5), while the concentrated water which had not permeated through the membrane was returned to rinse (4) and reused. Further, in order to shorten the crossover time between respective rinse processes there were provided with blades between tanks of rinse through which the photographic material passed.

| Color-developer (201) | Tank Solution | Replenisher |
|---|---|---|
| Water | 700 ml | 700 ml |
| Ethylenediaminetetraacetic acid | 1.5 g | 3.75 g |
| Sodium triisopropylnaphthalene-(β) sulfonate | 0.01 g | 0.01 g |
| Disodium 1,2-dihydroxybenzene-4,6-disulfonate | 0.25 g | 0.7 g |
| Triethanolamine | 5.8 g | 14.5 g |
| Potassium chloride | 10.0 g | — |
| Potassium bromide | 0.03 g | — |
| Potassium carbonate | 30.0 g | 39.0 g |
| Sodium sulfite | 0.14 g | 0.2 g |
| Disodium-N,N-bis(sulfonatoethyl)-hydroxylamine | 7.4 g | 15.0 g |
| 4-Amino-3-methyl-N-ethyl-N-(4-hydroxybutyl)-aniline · 2-p-toluenesulfonic acid | 14.5 g | 35.0 g |
| Water to make | 1,000 ml | 1,000 ml |
| pH (25° C.) | 10.05 | 11.60 |

Color developers (202), (203), (204), and (205) were prepared by adding respective fluorescent whitening agents shown below to color developer (201).

| Color developer | Fluorescent whitening agent | Added amount (g/liter) | |
|---|---|---|---|
| (202) | (B-1) | 2.0 | (Tank solution) |
| | " | 4.0 | (Replenisher) |
| (203) | (B-10) | 2.0 | (Tank solution) |
| | " | 4.0 | (Replenisher) |
| (204) | (SR-13) | 2.0 | (Tank solution) |
| | " | 4.0 | (Replenisher) |
| (205) | (SR-24) | 2.0 | (Tank solution) |
| | " | 4.0 | (Replenisher) |

The pH of each developer was adjusted to the same pH of tank solution or replenisher of color developer (201).

Bleach-fix solution (Two kinds of replenishers were used, wherein the components were separated, as shown (First replenisher)

| Water | 150 ml |

| | |
|---|---|
| Ethylenebisguanigine nitrate | 30 g |
| Ammonium sulfite monohydrate | 190 g |
| Ethylenediaminetetraacetic acid | 7.5 g |
| Ammonium bromide | 30 g |
| Ammonium thiosulfate (700 g/l) | 340 ml |
| Acetic acid (50%) | 250 ml |
| Water to make | 1,000 ml |
| pH (25° C.) | 6.0 |
| (Second replenisher) | | each characteristics curve, and the minimum densities were determined.

Further, residual rates of sensitizing dye in the color printing papers processed at unexposed state, were determined in the same manner as in Example 1.

Further, crystallization tests, in the same manner as in Example 1, for development replenishers (201) to (205) were conducted.

Results are shown in Table 2.

TABLE 2

| Color Developer No. | Fluorescent Whitening Agent No. | Residual Color Test | | Dmin (Yellow) | Crystallization Test (5° C., 5 Days) | Remarks |
|---|---|---|---|---|---|---|
| | | Residual Rate (%) Sensitizing Dye | | | | |
| | | A | B | | | |
| (201) | — | 78 | 80 | 0.18 | — | Comparative Example |
| (202) | (B-1) | 67 | 68 | 0.16 | Precipitates | " |
| (203) | (B-10) | 70 | 72 | 0.16 | " | " |
| (204) | (SR-13) | 37 | 39 | 0.10 | No Precipitate | This Invention |
| (205) | (SR-24) | 40 | 44 | 0.11 | " | " |

| | |
|---|---|
| Water | 140 ml |
| Ethylenediaminetetraacetic acid | 11.0 g |
| Fe (III) ammonium ethylenediaminetetraacetate | 715 g |
| Acetic acid (50%) | 100 ml |
| Water to make | 1,000 ml |
| pH (25° C.) | 3.3 |
| (Tank solution of bleach-fix) | |
| First replenisher | 300 ml |
| Second replenisher | 200 ml |
| Water to make | 1,000 ml |
| pH (25° C.) | 5.0 |
| Replenishing rate of bleach-fix (total 35 ml per m²) | |
| First replenisher | 21 ml |
| Second replenisher | 14 ml |

Rinse Solution

Ion-exchanged water (Ca and Mg each are 3 ppm or below)

Paper-processor used in this Example was one described in FIGS. 1 to 3 in JP-A No. 66540/1993, pp 45 to 46.

After the continuous processing according to the above processing process 3 was completed, color photographic printing papers gradation-exposed were subjected to a processing using each processing solution. Each of processed samples was determined, in the same manner as in Example 1, yellow reflective density, magenta reflective density, and cyan reflective density by As is apparent from the results in Table 2, the development processing solution according to the present invention does not bring out crystallization during the storage at a low temperature, and a white background less in residual color after processing by the color developer according to the present invention can be provided.

EXAMPLE 3

A continuous processing was conducted in the same manner as Processing process 2 in Example 1 using color developer (101) of Example 1. Running solution obtained after the continuous processing was subjected to residual color test, shown below, and crystallization test.

Processing solutions (301) to (310) were prepared by withdrawing each 200 ml of color developer and bleach-fix solution, after running test, and adding the fluorescent whitening agent as shown in Table 3. Unexposed color printing paper was processed by a small-size developing processor using processing solutions shown in Table 3. In the rinse steps, the same rinse solution as the running solution for rinsing in Example 2 was used.

After processing was completed, each processing solution and bleach-fix solution was observed the occurrence of precipitates in the same manner as in Example 1.

Results are shown in Table 4.

TABLE 3

| Processing Solution | Fluorescent Whitening Agent Used and Amount Added | | | |
|---|---|---|---|---|
| | Color Developer* | | Bleach-fix Solution** | |
| | Compound No. | Amount added (g/l) | Compound No. | Amount added (g/l) |
| (301) | B-1 | 2.0 | — | — |
| (302) | B-1 | 2.0 | B-1 | 1.0 |
| (303) | B-10 | 4.0 | — | — |
| (304) | ExB-2 | 4.0 | — | — |
| (305) | ExB-1 | 4.0 | — | — |
| (306) | SR-1 | 2.0 | SR-1 | 1.0 |
| (307) | SR-1 | 6.0 | — | — |
| (308) | SR-13 | 4.0 | — | — |
| (309) | SR-17 | 4.0 | — | — |
| (310) | SR-24 | 4.0 | — | — |

Note:
*Each 200 ml solution withdrawn from 2 liter of developer after the running test.
**Each 200 ml solution withdrawn from 2 liter of bleach-fix solution after the running test.

(ExB-1)

TABLE 3-continued

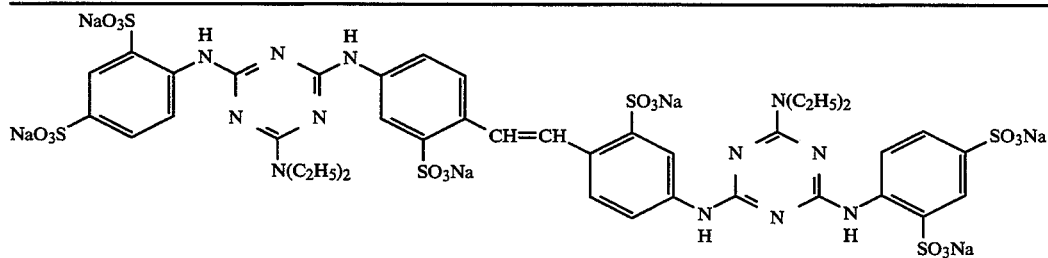

(ExB-2)

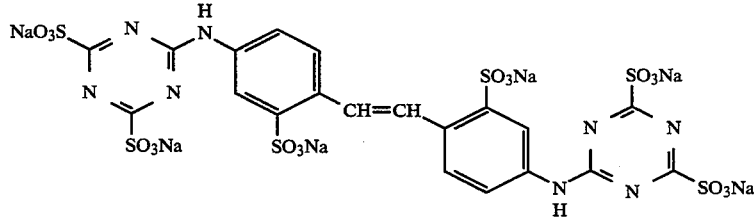

TABLE 4

| Processing solution No. | Residual Color Test Residual Rate (%) Sensitizing Dye | | Dmin (Yellow) | Crystallization Test (5° C., 5 Days) | | Remarks |
|---|---|---|---|---|---|---|
| | A | B | | Developer | Bleach-fix sln. | |
| (301) | 68 | 71 | 0.16 | Precipitates | No precipitate* | Comparative Example |
| (302) | 67 | 67 | 0.16 | " | Precipitates | " |
| (303) | 70 | 69 | 0.17 | " | No Precipitate* | " |
| (304) | 72 | 75 | 0.18 | " | "* | " |
| (305) | 85 | 84 | 0.19 | " | "* | " |
| (306) | 36 | 36 | 0.11 | No Precipitate | " | This Invention |
| (307) | 35 | 36 | 0.11 | " | "* | " |
| (308) | 33 | 37 | 0.10 | " | "* | " |
| (309) | 40 | 43 | 0.12 | " | "* | " |
| (310) | 36 | 38 | 0.11 | " | "* | " |

Note: *No precipitate was found since the fluorescent whitening agent was not added into the bleach-fix solution.

As is shown in Table 4, precipitates were occurred after storage at a low temperature in the replenisher of processing solutions (301) to (304), in which the conventional diaminostilbene compound was added. Further, the processing solution (305), in which a conventional diaminostilbene compound having an anilino group on triazine ring was added, did not bring out precipitates after the low temperature storage, but the residual color was the worst among tested samples. On the contrary, processing solutions according to the present invention did not bring out crystallization after the low temperature storage and attained the lowest residual color on the white background after processing.

EXAMPLE 4

The constitution of the present invention was applied to the processing for a color negative film as shown below.

A sample of multilayer color photographic material was prepared by multicoating compositions shown below on a triacetate cellulose film support provided with an under coat layer.

Compositions of Photosensitive Layers

Main materials used in each layer were classified as follows:
ExC: cyan coupler, UV: UV rays absorber,
ExM: magenta coupler, HBS: high-boiling organic solvent,
ExY: yellow coupler, H: gelatin hardening agent,
ExS: sensitizing dye.

Figures corresponding to each component represents the coating amount in terms of $g/m^2$ and for silver halide in terms of silver. With respect to sensitizing dyes, the coating amount is shown in mol per mol of silver halide in the same layer.

| First layer (Hallation-preventing layer) | |
|---|---|
| Black colloidal silver | silver 0.18 |
| Gelatin | 1.40 |
| ExM-1 | 0.18 |
| ExF-1 | $2.0 \times 10^{-3}$ |
| HBS-1 | 0.20 |
| Second layer (Intermediate layer) | |
| Silver iodobromide emulsion G | silver 0.065 |
| 2,5-di-t-pentadecylhydroquinone | 0.18 |
| ExC-2 | 0.020 |
| UV-1 | 0.060 |
| UV-2 | 0.080 |
| UV-3 | 0.10 |
| HBS-1 | 0.10 |
| HBS-2 | 0.020 |
| Gelatin | 1.04 |
| Third layer (Low sensitivity red-sensitive emulsion layer) | |
| Silver iodobromide emulsion A | silver 0.25 |
| Silver iodobromide emulsion B | silver 0.25 |
| ExS-1 | $6.9 \times 10^{-5}$ |
| ExS-2 | $1.8 \times 10^{-5}$ |
| ExS-3 | $3.1 \times 10^{-4}$ |
| ExC-1 | 0.17 |
| ExC-3 | 0.030 |
| ExC-4 | 0.10 |

-continued

| | |
|---|---|
| ExC-5 | 0.020 |
| ExC-7 | 0.0050 |
| ExC-8 | 0.010 |
| Cpd-2 | 0.025 |
| HBS-1 | 0.10 |
| Gelatin | 0.87 |

Fourth layer (Medium sensitivity red-sensitive emulsion layer)

| | |
|---|---|
| Silver iodobromide emulsion D | silver 0.70 |
| ExS-1 | $3.5 \times 10^{-4}$ |
| ExS-2 | $1.6 \times 10^{-5}$ |
| ExS-3 | $5.1 \times 10^{-4}$ |
| ExC-1 | 0.13 |
| ExC-2 | 0.060 |
| ExC-3 | 0.0070 |
| ExC-4 | 0.090 |
| ExC-5 | 0.025 |
| ExC-7 | 0.0010 |
| ExC-8 | 0.0070 |
| Cpd-2 | 0.023 |
| HBS-1 | 0.10 |
| Gelatin | 0.75 |

Fifth layer (High sensitivity red-sensitive emulsion layer)

| | |
|---|---|
| Silver iodobromide emulsion E | silver 1.40 |
| ExS-1 | $2.4 \times 10^{-4}$ |
| ExS-2 | $1.0 \times 10^{-4}$ |
| ExS-3 | $3.4 \times 10^{-4}$ |
| ExC-1 | 0.12 |
| ExC-3 | 0.045 |
| ExC-6 | 0.020 |
| ExC-8 | 0.025 |
| Cpd-2 | 0.050 |
| HBS-1 | 0.22 |
| HBS-2 | 0.10 |
| Gelatin | 1.20 |

Sixth layer (Intermediate layer)

| | |
|---|---|
| Cpd-1 | 0.10 |
| HBS-1 | 0.50 |
| Gelatin | 1.10 |

Seventh layer (Low sensitivity green-sensitive emulsion layer)

| | |
|---|---|
| Silver iodobromide emulsion C | silver 0.35 |
| ExS-4 | $3.0 \times 10^{-5}$ |
| ExS-5 | $2.1 \times 10^{-4}$ |
| ExS-6 | $8.0 \times 10^{-4}$ |
| ExM-1 | 0.010 |
| ExM-2 | 0.33 |
| ExM-3 | 0.086 |
| ExY-1 | 0.015 |
| HBS-1 | 0.30 |
| HBS-3 | 0.010 |
| Gelatin | 0.73 |

Eighth layer (Medium sensitivity green-sensitive emulsion layer)

| | |
|---|---|
| Silver iodobromide emulsion D | silver 0.80 |
| ExS-4 | $3.2 \times 10^{-5}$ |
| ExS-5 | $2.2 \times 10^{-4}$ |
| ExS-6 | $8.4 \times 10^{-4}$ |
| ExM-2 | 0.13 |
| ExM-3 | 0.030 |
| ExY-1 | 0.018 |
| HBS-1 | 0.16 |
| HBS-3 | $8.0 \times 10^{-3}$ |
| Gelatin | 0.90 |

Ninth layer (High sensitivity green-sensitive emulsion layer)

| | |
|---|---|
| Silver iodobromide emulsion E | silver 1.25 |
| ExS-4 | $3.7 \times 10^{-5}$ |
| ExS-5 | $8.1 \times 10^{-5}$ |
| ExS-6 | $3.2 \times 10^{-4}$ |
| ExC-1 | 0.010 |
| EXM-1 | 0.030 |
| ExM-4 | 0.040 |
| ExM-5 | 0.019 |
| Cpd-3 | 0.040 |
| HBS-1 | 0.25 |
| HBS-2 | 0.10 |
| Gelatin | 1.44 |

Tenth layer (Yellow filter layer)

| | |
|---|---|
| Yellow colloidal silver | silver 0.030 |
| Cpd-1 | 0.16 |
| HBS-1 | 0.60 |
| Gelatin | 0.60 |

Eleventh layer (Low sensitivity blue-sensitive emulsion layer)

| | |
|---|---|
| Silver iodobromide emulsion C | silver 0.18 |
| ExS-7 | $8.6 \times 10^{-4}$ |
| ExY-1 | 0.020 |
| ExY-2 | 0.22 |
| ExY-3 | 0.50 |
| ExY-4 | 0.020 |
| HBS-1 | 0.28 |
| Gelatin | 1.10 |

Twelfth layer (Medium sensitivity blue-sensitive emulsion layer)

| | |
|---|---|
| Silver iodobromide emulsion D | silver 0.40 |
| ExS-7 | $7.4 \times 10^{-4}$ |
| ExC-7 | $7.0 \times 10^{-3}$ |
| ExY-2 | 0.050 |
| ExY-3 | 0.10 |
| HBS-1 | 0.050 |
| Gelatin | 0.78 |

Thirteenth layer (High sensitivity blue-sensitive emulsion layer)

| | |
|---|---|
| Silver iodobromide emulsion F | silver 1.00 |
| ExS-7 | $4.0 \times 10^{-4}$ |
| ExY-2 | 0.10 |
| ExY-3 | 0.10 |
| HBS-1 | 0.070 |
| Gelatin | 0.86 |

Fourteenth layer (First protective layer)

| | |
|---|---|
| Silver iodobromide emulsion G | silver 0.20 |
| UV-4 | 0.11 |
| UV-5 | 0.17 |
| HBS-1 | $5.0 \times 10^{-2}$ |
| Gelatin | 1.00 |

Fifteenth layer (Second protective layer)

| | |
|---|---|
| H-1 | 0.40 |
| PB-1 (diameter: 1.7 μm) | $5.0 \times 10^{-2}$ |
| PB-2 (diameter: 1.7 μm) | 0.10 |
| PB-3 | 0.10 |
| S-1 | 0.20 |
| Gelatin | 1.20 |

Further, in order to improve preservability, processability, pressure resistance, antimold and antibacterial properties, antistatic property, and coating property, compounds of W-1 to W-3, B-4 to B-6, and F-1 to F-17, and salts of iron, lead, gold, platinum, iridium, and rhodium were suitably added in each layer.

Details of emulsions used in this Example are shown in Table 5.

In Table 5, (1) Emulsions A to F were subjected to a reduction sensitization using thiourea dioxide and thiosulfonic acid at preparation of grains, according to the Example described in JP-A No. 191938/1990.

(2) Emulsions A to F were subjected to a gold sensitization, a sulfur sensitization, and a selenium sensitization under the presence of respective sensitizing dyes described in each layer and sodium thiocyanate, according to Example described in JP-A No. 237450/1991.

(3) At the preparation of tabular grains, low-molecular-weight gelatin was used according to Example described in JP-A No. 158426/1989.

(4) Tabular grains and normal crystal grains having grain structure were observed a rearrangement line by a high-pressure electron microscope, as described in JP-A No. 237450/1991.

TABLE 5

|  | Average AgI content (%) | Grain Size Average Diameter (μm) | Deviation coefficient (%) | Ratio of Diameter/ Thickness | Ratio of silver amount [core/shell] or [core/intermediate/shell] | (AgI content %) | Grain structure and shape |
| --- | --- | --- | --- | --- | --- | --- | --- |
| Emulsion A | 4.0 | 0.45 | 27 | 1 | [1/3] | (13/1) | Double structure octahedral grains |
| Emulsion B | 8.9 | 0.70 | 14 | 1 | [3/7] | (25/2) | Double structure octahedral grains |
| Emulsion C | 2.0 | 0.55 | 25 | 7 | — |  | Uniform structure tabular grains |
| Emulsion D | 9.0 | 0.65 | 25 | 6 | [12/59/29] | (0/11/8) | Triple structure tabular grains |
| Emulsion E | 9.0 | 0.85 | 23 | 5 | [8/59/33] | (0/11/8) | Triple structure tabular grains |
| Emulsion F | 14.5 | 1.25 | 25 | 3 | [37/63] | (34/3) | Double structure tabular grains |
| Emulsion G | 1.0 | 0.07 | 15 | 1 | — |  | Uniform structure |

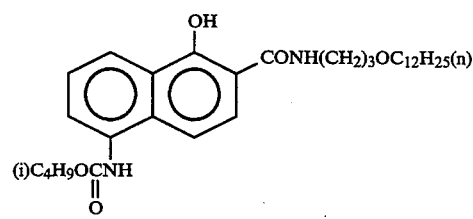

ExC-1

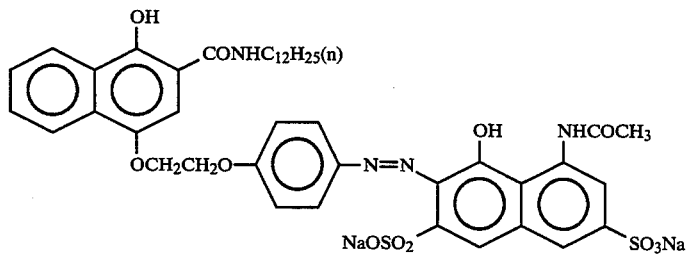

ExC-2

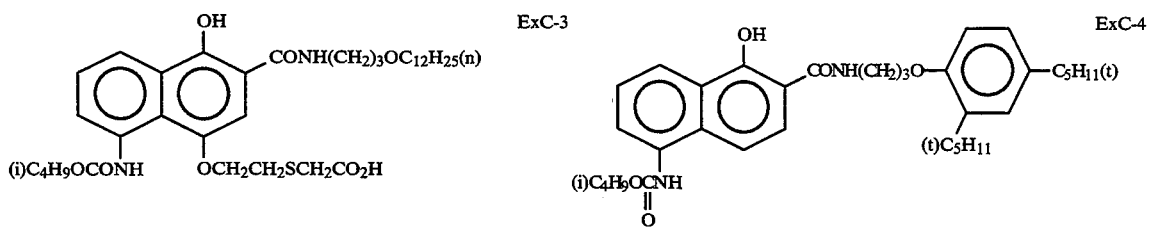

ExC-3     ExC-4

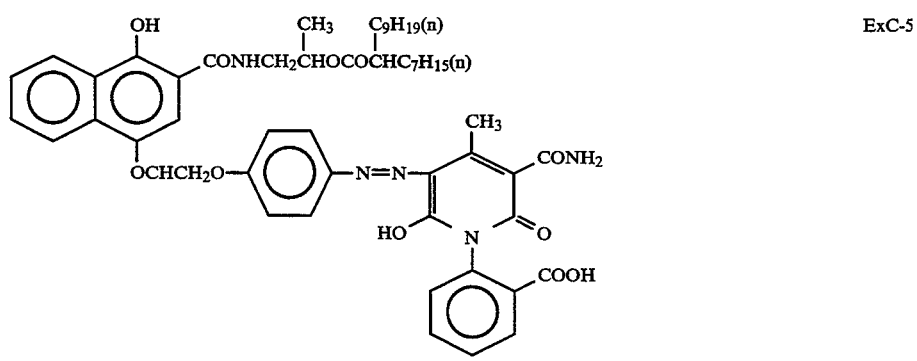

ExC-5

ExC-6
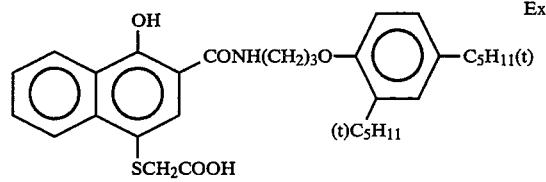
ExC-7
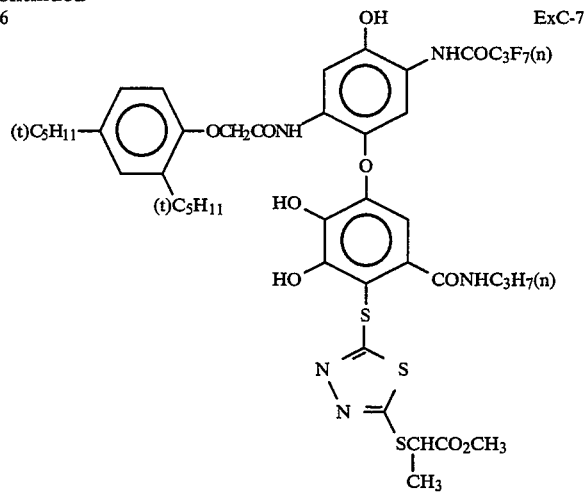
ExC-8
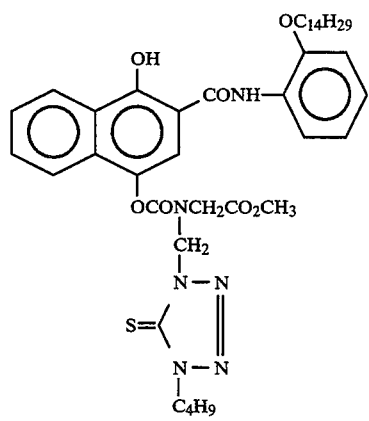
ExM-1
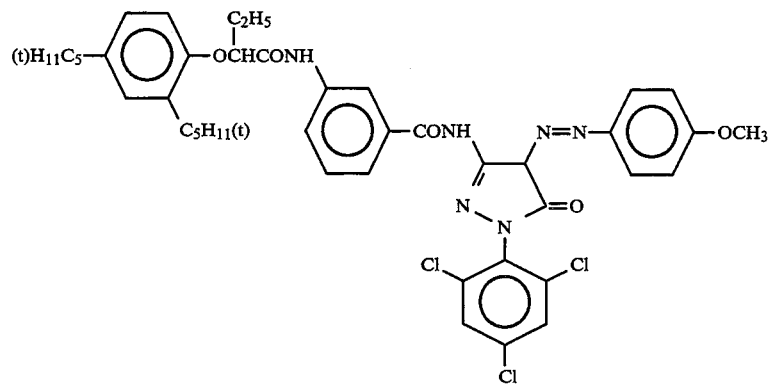
ExM-2
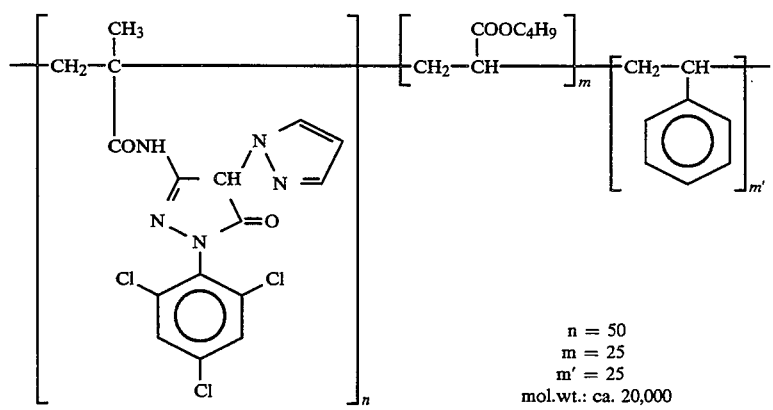
n = 50
m = 25
m' = 25
mol.wt.: ca. 20,000

-continued
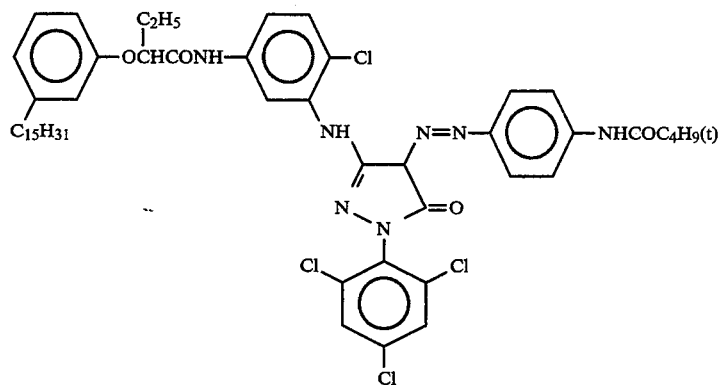
ExM-3
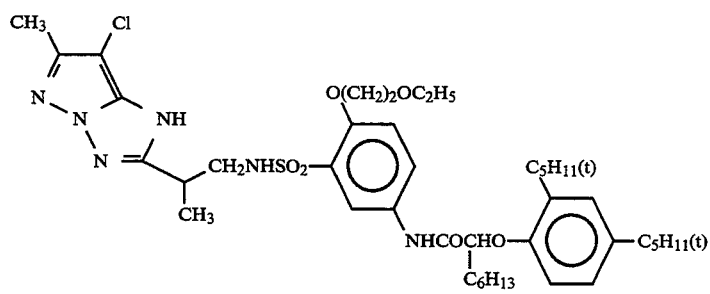
ExM-4
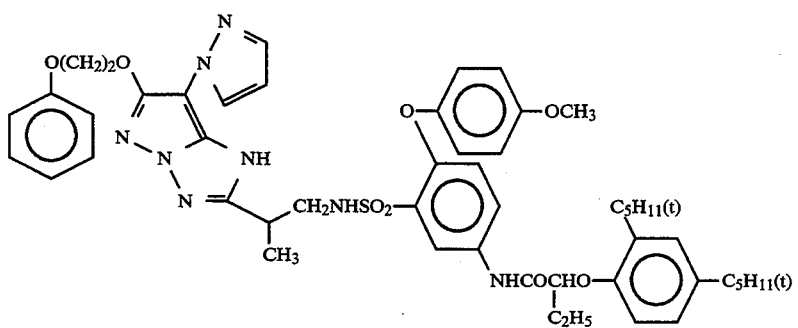
ExM-5
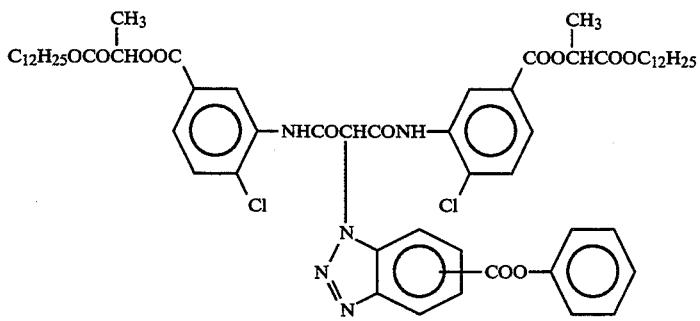
ExY-1
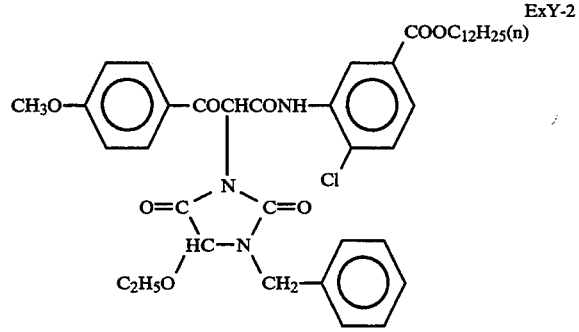
ExY-2
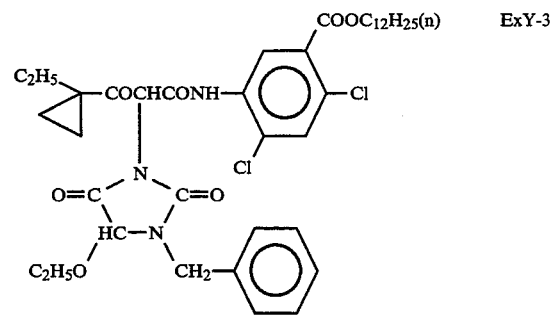
ExY-3

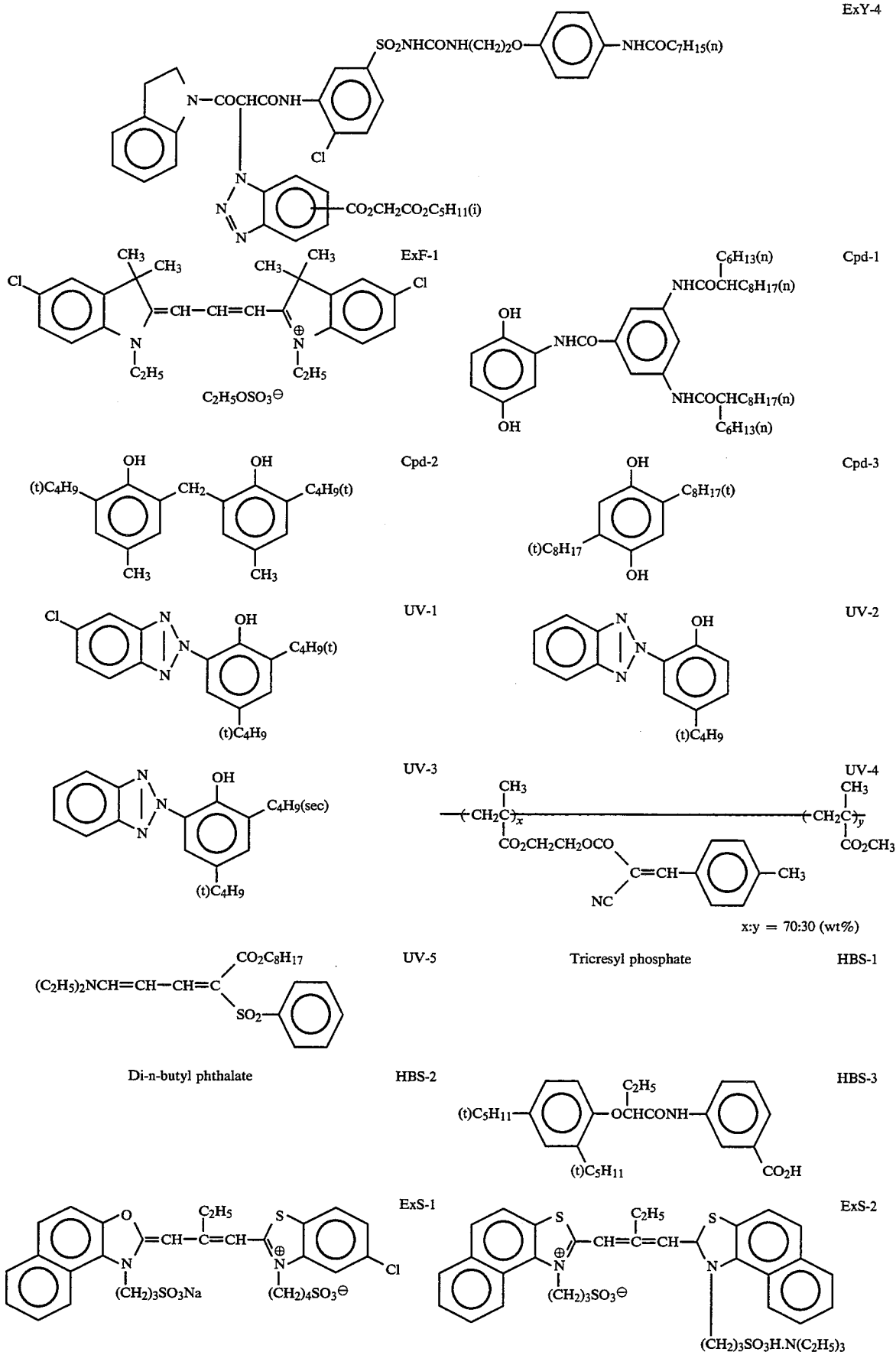

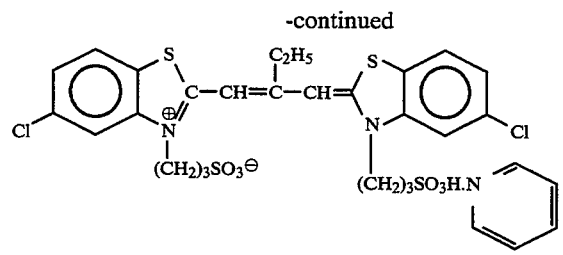
ExS-3
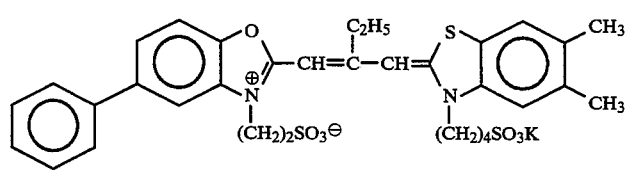
ExS-4
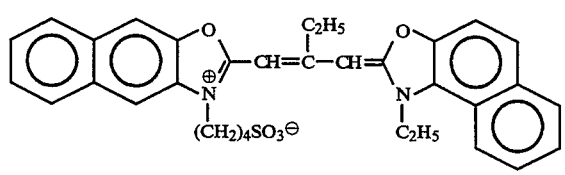
ExS-5
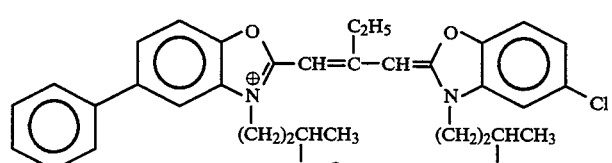
ExS-6
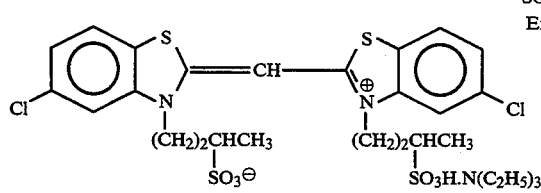
ExS-7
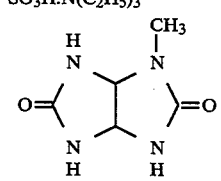
S-1
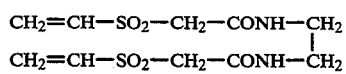
H-1
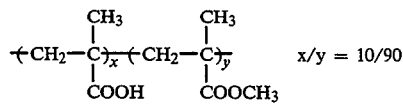
PB-1    x/y = 10/90
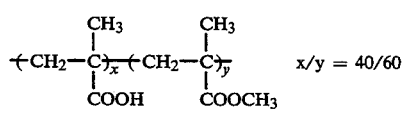
PB-2    x/y = 40/60
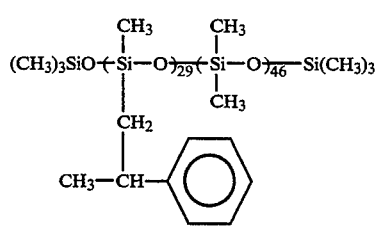
PB-3
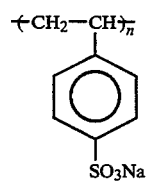
PB-4
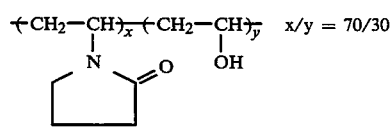
PB-5    x/y = 70/30
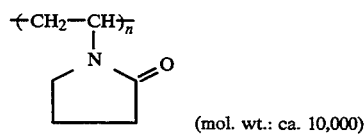
PB-6
(mol. wt.: ca. 10,000)
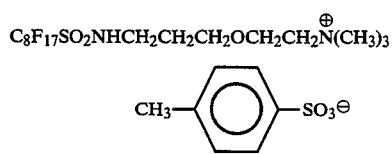
W-1

-continued
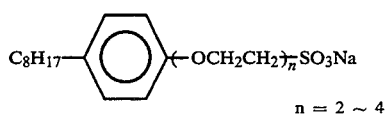 W-2
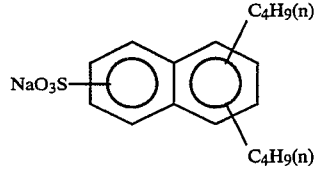 W-3
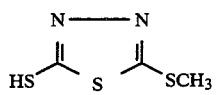 F-1
n = 2 ~ 4
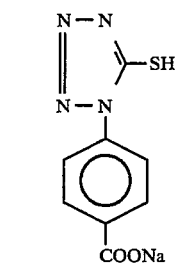 F-2
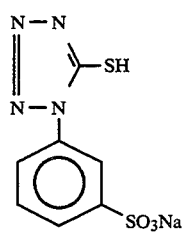 F-3
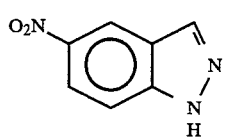 F-4
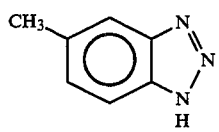 F-5
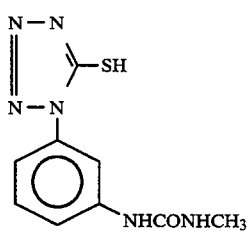 F-6
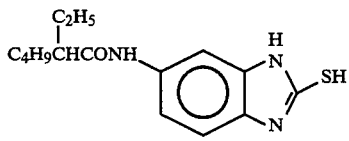 F-7
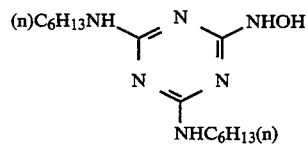 F-8
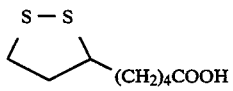 F-9
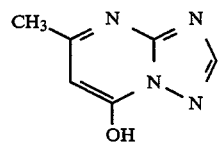 F-10
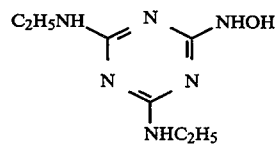 F-11
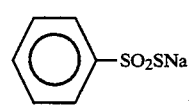 F-12
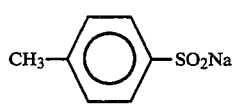 F-13
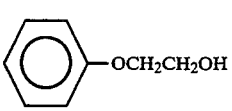 F-14
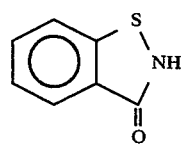 F-15
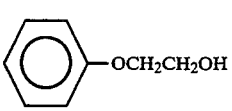 F-16

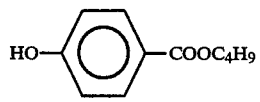

F-17

The thus prepared samples were exposed to light imagewisely and were processed continuously with the below-mentioned processing solutions until the replenishment amount of the bleach-fix solution reached 10 times the volume of the tank.

The bleach-fix solution was subjected to in-line recovering of silver by using a silver-recovering apparatus, and the solution obtained by recovering silver was reprocessed and was used again as a replenishing solution of the bleach-fix solution. As the silver-recovering apparatus, a small-sized electrolysis silver-recovering apparatus was used, in which the anode is made of carbon and the cathode is a stainless drum with the current density being 0.5 A/dm$^2$. Details of the apparatus used in the system of recovering silver are described in FIG. 1 in Japanese Patent Application No. 329240/1992.

The overflow of the bleach-fix solution was directly fed to the silver-recovering apparatus, and the liquid obtained after the electrolysis treatment was returned to the original bleach-fix bath through a filter by a pump 1.

The overflow from the silver-recovering apparatus is recovered into a recovering tank in an amount of 600 ml per liter of the overflow; then when the recovered amount reached 1 liter, after air was blown into it for about 2 hours and a regenerant was added, it was fed to the replenishing tank of the bleach-fix solution by a pump 2. The remaining solution was discharged, and after silver was separately recovered therefrom, it was discharged as waste liquor. The amount of the waste liquor was 196 ml per m$^2$ of processed Sample 101.

The washing with water was carried out in a countercurrent cascade manner by arranging horizontally a 5-stage multi-chamber washing tank. The overflow from the first water for washing was cascaded to the preceding bath; that is, the bleach-fix bath. Between the fourth washing and the fifth washing, a reverse osmosis apparatus RC 30 (manufactured by Fuji Photo Film Co., Ltd.) was placed. The processing steps are shown below. Details of the processor used are described in FIG. 2 in Japanese Patent Application No. 329240/1992.

| Processing step | Time | Temperature | Replenisher* | Tank Volume |
|---|---|---|---|---|
| Color developing | 60 sec | 48.5° C. | 80 ml | 2 liter |
| Bleach-fixing | 60 sec | 48.5° C. | 200 ml | 2 liter |
| Rinse (1) | 15 sec | 45° C. | — | 0.5 liter |
| Rinse (2) | 15 sec | 45° C. | — | 0.5 liter |
| Rinse (3) | 15 sec | 45° C. | — | 0.5 liter |
| Rinse (4) | 15 sec | 45° C. | — | 0.5 liter |
| Rinse (5) | 15 sec | 45° C. | 104 ml | 0.5 liter |
| Stabilizing | 2 sec | R.M. | 30 ml | painting |
| Drying | 50 sec | 80° C. | | |

Note: *Replenisher amount per m$^2$ of photographic material.

The crossover time from the color development to the bleach-fix and from the bleach-fix to the first washing was 3 sec. The average carryover per m$^2$ of the photographic material was 68 ml.

To compensate for the evaporation of each bath, the temperature and humidity outside the processor were detected as described in JP-A No. 280042/1991, and the evaporation loss was calculated for the compensation.

As the water for the compensation of the evaporation, deionized water for the above water for washing was used.

The composition of each processing solution is as followed, respectively:

| | Mother Solution (g) | Replenisher (g) |
|---|---|---|
| Color-developer | | |
| Diethylenetriaminepentaacetic acid | 4.0 | 4.0 |
| 1-Hydroxyethylidene-1,1-diphosphonic acid | 2.7 | 3.0 |
| Potassium hydroxide | 3.0 | 4.5 |
| Sodium sulfite | 4.0 | 9.5 |
| Sodium bicarbonate | 1.8 | — |
| Potassium carbonate | 31.7 | 39.0 |
| Potassium bromide | 6.5 | — |
| Potassium iodide | 1.3 mg | — |
| N-Methylhydroxylamine hydrochloride | 5.0 | 9.0 |
| 2-Methyl-4-[N-ethyl-N-($\beta$-hydroxyethyl)-amino]aniline sulfonate | 13.0 | 24.0 |
| Water to make | 1.0 liter | 1.0 liter |
| pH (25° C.) | 10.05 | 12.10 |
| Bleach-fix solution | | at start |
| Fixing agent (Compound A) | 1.8 mol | 2.97 mol |

$$\text{CH}_3-\underset{\underset{\text{CH}_3}{|}}{\overset{\oplus}{N}}\diagup\overset{N=\!\!=\!\!N}{\phantom{x}}\diagdown\text{S}^\ominus$$

| | | |
|---|---|---|
| Iron (III) ammonium 1,3-propylene-diaminetetraacetate monohydrate | 144.0 | 237.6 |
| Ammonium bromide | 40.0 | 66.0 |
| Ammonium nitrate | 20.0 | 33.0 |
| Water to make | 1.0 liter | 1.0 liter |
| pH (25° C.) | 4.5 | 4.4 |
| (pH was adjusted by acetic acid and aqueous ammonium) | | |
| Regenerating agent for bleach-fix solution | | |
| Added amount (g) per liter of recovered solution for regeneration | | |
| Iron (III) ammonium 1,3-propylene-diaminetetraacetate monohydrate | 93.6 | |
| Fixing agent (compound A) | 1.17 mol | |
| Ammonium bromide | 26 | |
| Ammonium nitrate | 13 | |

Washing Solution

Both Tank Solution and Replenisher

Tap water was treated by passing through a mixed bed ion-exchange column filled with H-type strong acidic cation exchange resin (Amberlite IR-120B, tradename manufactured by Rohm & Haas) and OH-type strong basic anion exchange resin (Amberlite IR-400, the same as the above) so that the concentrations of calcium ions and magnesium ions decrease both to 3 mg/liter or below. To the thus-obtained ion-exchanged water 20 mg/liter of sodium dichlorinated isocyanurate and 150 mg/liter of sodium sulfate were added. The pH of this solution was in a range of 6.5 to 7.5.

| Stabilizing solution (Both tank solution and replenisher) | (g) |
| --- | --- |
| Sodium p-toluenesulfinate | 0.03 |
| Polyoxyethylene-p-monononyl phenyl ether (av. polymerization degree: 10) | 0.2 |
| Disodium ethylenediaminetetraacetate | 0.05 |
| 1,2-benzoisothiazoline-3-one | 0.03 |
| 1,2,4-triazole | 1.3 |
| 1,4-bis(1,2,4-triazole-1-yl-methyl)piperazine | 0.75 |
| Water to make | 1.0 liter |
| pH | 8.5 |

The waste solution volume after processing 100 m² of the above described sample by the above processing process was 19.6 liter. This volume corresponds to about one thirteenth of total waste solution volume (about 250 liter) in the CN-16 FA system for color negative films processing by Fuji Photo Film Co., Ltd., which system is an example of a conventional processing system, thereby showing that the waste solution volume is remarkably reduced.

After the above continuous processing was completed, the same processing and tests of residual color and crystallization using running solutions as those in Example 3 were conducted. As the results, the similar results to Example 3 were obtained.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method for forming an image, in which method, after a silver halide photographic material having a photosensitive silver halide emulsion layer on at least one side of a support is exposed to light imagewise, the silver halide photographic material is subjected to a developing step, a desilvering step, a washing and/or stabilizing step, and then the material is dried, which comprises at least one step of the above processing steps being carried out in the presence of at least one compound represented by the following formula (I):

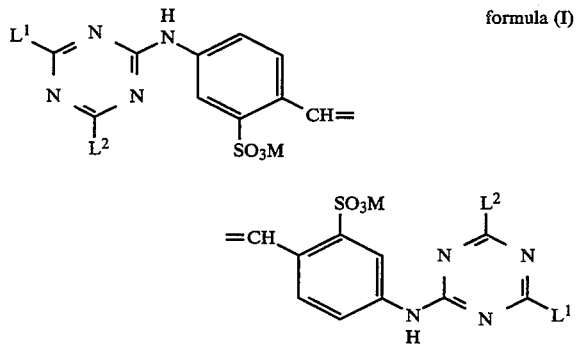

formula (I)

wherein
L¹ and L², which are the same or different, each represent —OR¹ or —N—R²(R³), wherein the four substituents L¹ and L² have four or more substituents in total selected from the group consisting of substituents represented by the following formula (II);

R¹ and R² each represent a hydrogen atom, an alkyl group, or an alkyl group having a substituent selected from the group consisting of substituents represented by the following formula (II);

R³ represents an alkyl group or an alkyl group having a substituent selected from the group consisting of substituents represented by the following formula (II); and M represents a hydrogen atom, an alkali metal, an ammonium, or a pyridinium:

formula (II)

—SO₃M, —OSO₃M, —COOM, and —NR₃X wherein
X represents a halogen atom,
R represents an alkyl group, and
M has the same meaning as M in formula (I).

2. The method for forming an image as claimed in claim 1, wherein a color developer containing, as a color developing agent, a compound represented by the following formula (D) is used in the developing step:

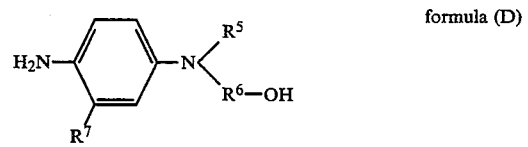

formula (D)

wherein
R⁵ represents a straight-chain or branched-chain alkyl group having 1 to 6 carbon atoms, or a straight-chain or branched-chain hydroxylalkyl group having 3 to 6 carbon atoms;

R⁶ represents a straight-chain or branched-chain alkylene group having 3 to 6 carbon atoms, or a straight-chain or branched-chain hydroxylalkylene group having 3 to 6 carbon atoms; and R⁷ represents a hydrogen atom, a straight-chain or branched-chain alkyl group having 1 to 4 carbon atoms, or a straight-chain or branched-chain alkoxy group having 1 to 4 carbon atoms.

3. The method for forming an image as claimed in claim 1, wherein the substituents L¹ and L² of formula (I) each are selected from the group consisting of a methoxy group, an ethoxy group, a propoxy group, an isopropoxy group, a butoxy group, an isobutoxy group, a pentyloxy group, a hexyloxy group, a methylamino group, an ethylamino group, a propylamino group, an isopropylamino group, a butylamino group, an isobutylamino group, a 2-hydroxyethoxy group, a 3-hydroxypropoxy group, a 4-hydroxybutoxy group, a 2-hydroxyethylamino group, a 3-hydroxypropylamino group, a 4-hydroxybutylamino group, a 2-hydroxyethylethylamino group, a 3-hydroxypropylpropylamino group, a 4-hydroxybutylbutylamino group, a dimethylamino group, a diethylamino group, a dipropylamino group, a diisopropylamino group, a dibutylamino group, diisobutylamino group, a di-2-hydroxyethylamino group, a di-3-hydroxypropylamino group, a dihydroxybutylamino group, a 2-sulfoethoxy group, a 3-sulfopropoxy group, a 4-sulfobutoxy group, a 2-sulfoethylamino group, a 3-sulfopropylamino group, a 4-sulfobutylamino group, a di-2-sulfoethylamino group, a di-3-sulfopropylamino group, a di-4-sulfobutylamino group, a 2-sulfoethylmethylamino group, a 3-sulfopropylmethylamino group, a 4-sulfobutylmethylamino group, a 2-sulfoethylethylamino group, a 3-sulfopropylethylamino group, a 4-sulfobutylethylamino group, a carboxymethoxy group, a 2-carboxyethoxy group, a 3-carboxypropoxy group, a 4-carboxybutoxy group, a carboxymethylamino group, a 2-carboxyethylamino group, a 3-carboxypropylamino group, a 4-carboxybutylamino group, a di-2-carboxyethylamino group, a di-3-carboxypropylamino group, a di-4-carboxybutylamino group, a 2-carboxyethylmethylamino group, a 3-carboxypropylmethylamino group, a 4-carboxybutylmethylamino group, a 2-carboxyethylethylamino group, a 3-carboxypropylethylamino group, a 4-carboxybutylethylamino group, a 2-sulfoxyethoxy group, a 3-sulfoxypropoxy group, a 4-sulfoxybutoxy group, a 2-sulfoxyethylamino group, a 3-sulfoxypropylamino group, a 4-sulfoxybutylamino group, a di-2-sulfoxyethylamino group, a di-3-sulfoxypropylamino group, a di-4-sulfoxybutylamino group, a 2-sulfoxyethylmethylamino group, a 3-sulfoxypropylmethylamino group, a 4-sulfoxybutylmethylamino group, a 2-sulfoxyethylethylamino group, a 3-sulfoxypropylethylamino group, a 4-sulfoxybutylethylamino group, a trimethylammoniomethylamino group, a trimethylammonioethylamino group, a trimethylammoniopropylamino group, a triethylammoniomethylamino group, a triethylammonioethylamino group, and a triethylammoniopropylamino group.

4. The method for forming an image as claimed in claim 1, wherein the four substituents $L^1$ and $L^2$ of the compound represented by formula (I) have 4 to 8 substituents in total selected from the group consisting of substituents represented by formula (II).

5. The method for forming an image as claimed in claim 1, wherein the silver halide photographic material to be processed is a color negative films or a color photographic paper.

6. The method for forming an image as claimed in claim 1, wherein the silver halide photographic material comprises a high-silver-chloride emulsion whose silver chloride content is 90 mol % or more, and the silver halide photographic material is processed rapidly at a low-replenishing-rate.

7. The method for forming an image as claimed in claim 1, wherein the compound represented by formula (I) is used in combination with the compound represented by the following formula (III):

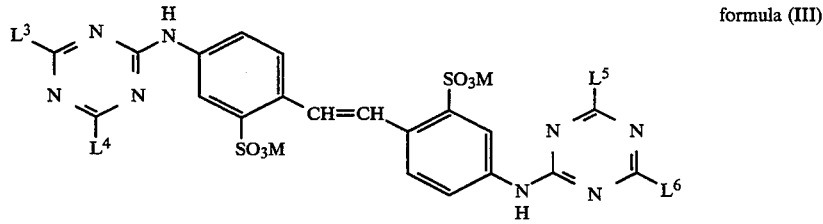

formula (III)

wherein
$L^3$, $L^4$, $L^5$, and $L^6$, which are the same or different, each represent —$OR^8$ or —N—$R^9(R^{10})$, wherein $R^8$, $R^9$, and $R^{10}$ each represent a hydrogen atom an alkyl group, a substituted alkyl group, or an alkyl group having a substituent selected from the group consisting of substituents represented by the following formula (IV), and M represents a hydrogen atom, an alkali metal, an ammonium, or a pyridinium, wherein four substituents $L^3$, $L^4$, $L^5$, and $L^6$ do not have four or more substituents in total, selected from the group consisting of substituents represented by the above formula (IV)
formula (IV)
—$SO_3M$, —$OSO_3M$, —COOM, —$NR_3X$
wherein
X represents a halogen atom,
R represents an alkyl group, and
M has the same meaning as M in formula (III).

8. The method for forming an image as claimed in claim 1, wherein the compound represented by formula (I) is used in a color developer or a black-and-white developer.

9. The method for forming an image as claimed in claim 1, wherein the concentration of the compound represented by formula (I) in the processing solution is $5 \times 10^{-5}$ to $1 \times 10^{-2}$ mol/liter.

10. The method for forming an image as claimed in claim 2, wherein the compound represented by formula (D) is selected from the group consisting of 4-amino-N-ethyl-N-(3-hydroxypropyl)-3-methylaniline and 4-amino-N-ethyl-(4-hydroxybutyl)-3-methylaniline.

* * * * *